(12) United States Patent
Schwardt et al.

(10) Patent No.: US 8,403,937 B2
(45) Date of Patent: Mar. 26, 2013

(54) APPARATUS AND METHOD FOR MEDICAL PROCEDURES WITHIN A SPINE

(75) Inventors: Jeffrey D. Schwardt, Palo Alto, CA (US); Brian Donovan, San Jose, CA (US); Andrew Kohm, Burlingame, CA (US); Hugues F. Malandain, Mountain View, CA (US); Erika I. Palmer, Menlo Park, CA (US); Mike Smith, San Jose, CA (US); Eric Wong, Mountain View, CA (US)

(73) Assignee: Kyphon Sarl, Neuchatel (CH)

( * ) Notice: Subject to any disclaimer, the term of this patent is extended or adjusted under 35 U.S.C. 154(b) by 1504 days.

(21) Appl. No.: 11/694,257

(22) Filed: Mar. 30, 2007

(65) Prior Publication Data
US 2008/0249603 A1  Oct. 9, 2008

(51) Int. Cl.
- A61B 17/58 (2006.01)
- A61B 17/60 (2006.01)
- A61B 17/88 (2006.01)
- A61F 2/00 (2006.01)

(52) U.S. Cl. .......................................... 606/92; 606/279
(58) Field of Classification Search ................ 606/86 R, 606/92–95
See application file for complete search history.

(56) References Cited

U.S. PATENT DOCUMENTS

| | | | |
|---|---|---|---|
| 4,083,369 A | 4/1978 | Sinnreich | |
| 4,313,434 A | 2/1982 | Segal | |
| 4,327,736 A | 5/1982 | Inoue | |
| 4,969,888 A | 11/1990 | Scholten et al. | |
| 5,108,404 A | 4/1992 | Scholten et al. | |
| 5,254,091 A | 10/1993 | Aliahmad | |
| 5,439,447 A | 8/1995 | Miraki | |
| 5,468,245 A * | 11/1995 | Vargas, III | 606/94 |
| 5,762,629 A | 6/1998 | Kambin | |
| 6,241,734 B1 | 6/2001 | Scribner et al. | |
| 6,245,046 B1 | 6/2001 | Sibbitt | |
| 6,248,110 B1 * | 6/2001 | Reiley et al. | 606/93 |
| 6,423,083 B2 | 7/2002 | Reiley et al. | |
| 6,716,216 B1 | 4/2004 | Boucher et al. | |
| 6,740,093 B2 | 5/2004 | Hochschuler et al. | |
| 6,899,719 B2 | 5/2005 | Reiley et al. | |
| 7,001,431 B2 | 2/2006 | Bao et al. | |
| 7,815,649 B2 * | 10/2010 | Layne et al. | 606/105 |

(Continued)

FOREIGN PATENT DOCUMENTS

| | | |
|---|---|---|
| JP | 8038618 | 2/1996 |
| WO | 9856301 | 12/1998 |

OTHER PUBLICATIONS

International Search Report and Written Opinion for PCT/US08/058119, mailed on Jul. 17, 2008; 10 pages.

*Primary Examiner* — Anu Ramana
(74) *Attorney, Agent, or Firm* — Dilworth & Barrese, LLP

(57) ABSTRACT

Devices and methods for performing a procedure within a spine are disclosed herein. In one embodiment, a method includes expanding an expandable member to move a tissue portion and form a cavity within an interior of a bone-related structure. At least a portion of the cavity is filled with a filler material while simultaneously withdrawing a medium from the expandable member at a predefined ratio such that the tissue portion substantially maintains its moved position. In some embodiments, the predefined ratio is 1:1. In another embodiment, a method includes expanding an expandable member to move a tissue portion and form a cavity within an interior of an intervertebral disc. At least a portion of the cavity is filled with a filler material while substantially maintaining the moved position of the tissue portion.

19 Claims, 25 Drawing Sheets

U.S. PATENT DOCUMENTS

2004/0024410 A1 2/2004 Olson, Jr. et al.
2004/0098015 A1 5/2004 Weikel et al.
2004/0210231 A1 10/2004 Boucher et al.
2005/0021084 A1* 1/2005 Lu et al. .................... 606/218

* cited by examiner

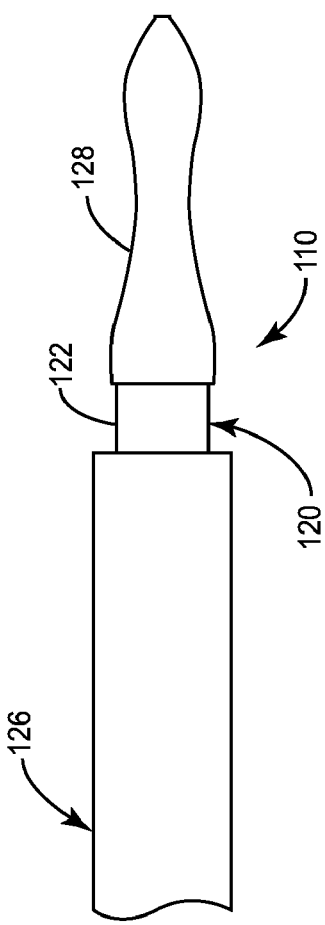
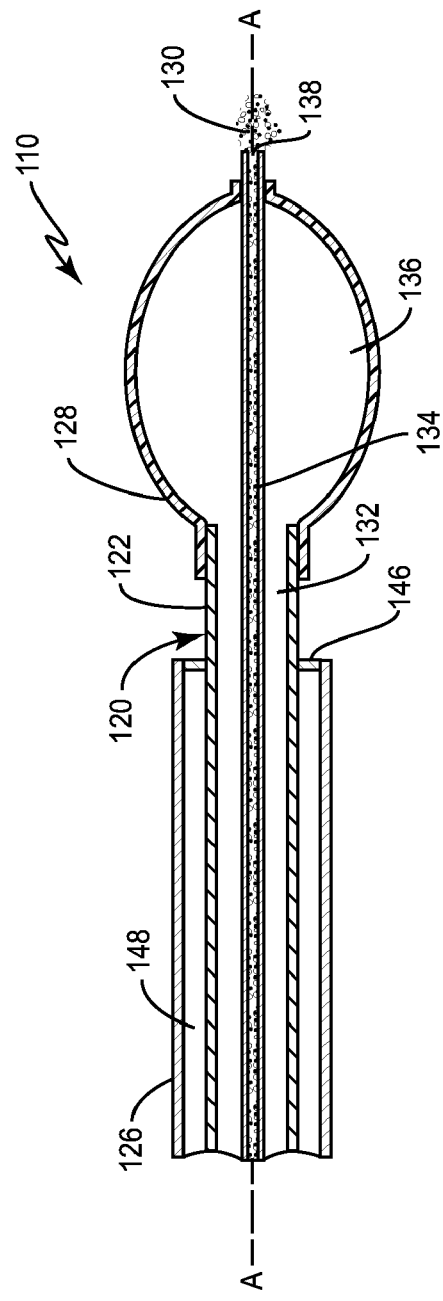

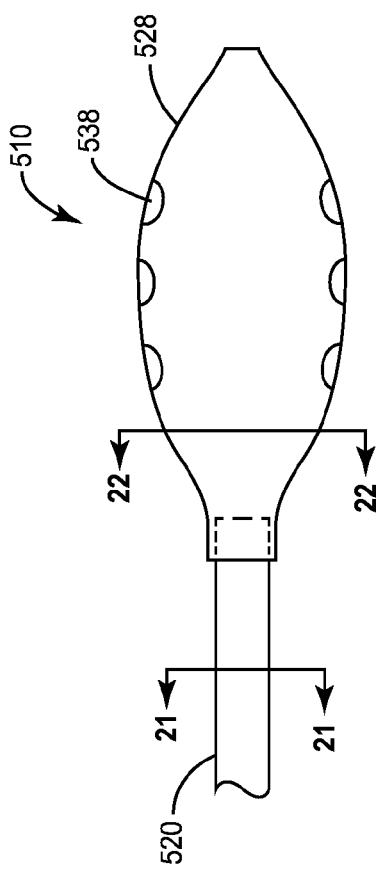
FIG. 20
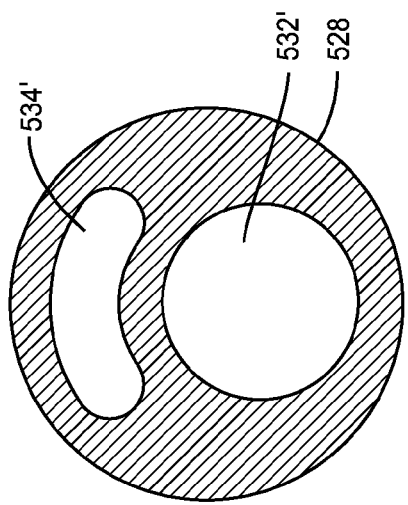
FIG. 22
FIG. 21

US 8,403,937 B2

APPARATUS AND METHOD FOR MEDICAL PROCEDURES WITHIN A SPINE

CROSS-REFERENCE TO RELATED APPLICATIONS

This application is related to U.S. patent application, entitled "Apparatus and Methods for Medical Procedures within a Spine," Ser. No. 11/694,289, filed on same date, the entire disclosure of which is hereby incorporated by reference in its entirety.

BACKGROUND

The invention relates generally to medical devices and procedures, including, for example, medical devices and methods for percutaneous treatment within a spine.

Known medical devices are configured to access percutaneously a vertebra, intervertebral disc, or other areas of a spine to perform a variety of different medical procedures. For example, some devices are configured to distract an interior area of a disc or vertebra. Other devices are configured to inject a filler or replacement material into the distracted volume. In such known medical procedures, separate devices are typically used to distract and fill a disc or vertebra. In such medical procedures, however, the distracted volume (e.g., distracted height) within the vertebra or disc can be reduced during the changing of medical devices.

Thus, a need exists for an apparatus and method for performing procedures within a spine that can distract an interior region of the spine or expand a tissue cavity in or near the spine, and also provide for the injection of a filler material with the same device while maintaining the distracted height or size of the cavity.

SUMMARY OF THE INVENTION

Devices and methods for performing a procedure within a spine are disclosed herein. In one embodiment, a method includes expanding an expandable member to move a tissue portion and form a cavity within an interior of a bone-related structure. At least a portion of the cavity is filled with a filler material while simultaneously withdrawing a medium from the expandable member at a predefined ratio such that the tissue portion substantially maintains its moved position. In some embodiments, the predefined ratio is 1:1. In another embodiment, a method includes expanding an expandable member to move a tissue portion and form a cavity within an interior of an intervertebral disc. At least a portion of the cavity is filled with a filler material while substantially maintaining the moved position of the tissue portion.

BRIEF DESCRIPTION OF THE DRAWINGS

FIG. 2 is a side view of a portion of an embodiment of a medical device shown in a collapsed configuration and disposed partially within, an extending from, a portion of an access cannula.

FIG. 3 is a side cross-sectional view of the medical device and access cannula of FIG. 2 with the medical device shown in an expanded configuration.

FIG. 20 is a side view of a portion of a medical device according to another embodiment.

FIG. 21 is a cross-sectional view of the medical device of FIG. 20 taken along line 21-21 in FIG. 20.

FIG. 22 is a cross-sectional view of the medical device of FIG. 20 taken along line 22-22 in FIG. 20.

DETAILED DESCRIPTION

Figure 1:
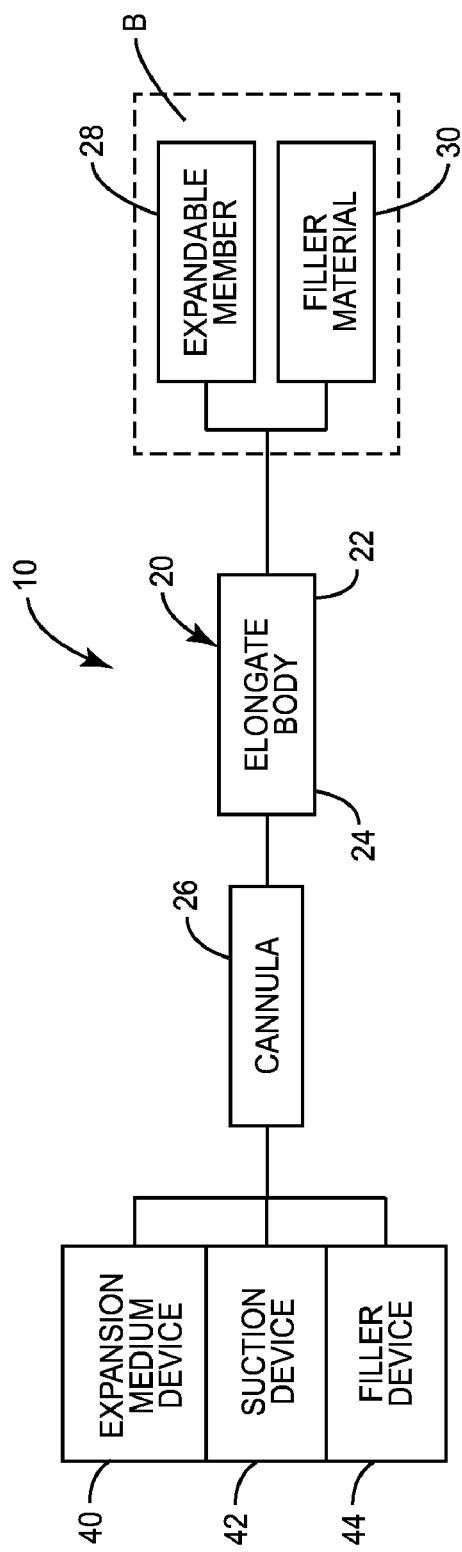
FIG. 1 is a schematic illustration of various medical devices that can be used in a method according to embodiments of the invention.

Devices and methods for performing medical procedures are disclosed herein. In one variation, a method provides for the distraction of a tissue portion within an interior of a bone-related structure (e.g., an intervertebral disc or a vertebra) forming a cavity within the bone-related structure. A filler material (e.g., hydrogel or bone cement) is then deposited within at least a portion of the cavity while maintaining the distracted position of the tissue portions. A medical device is described herein that can provide for both the distraction of the bone-related structure and the delivery of the filler material. For example, a medical device can include two lumens, one for actuating a distraction member (e.g., an expandable member), the other for delivering the filler material. In some embodiments, the distraction is performed by expanding an expandable member via a first lumen of the expandable member, and the filler material is deposited via a second lumen of the expandable member. In some embodiments, after the filler material has been deposited within the cavity, the expandable member can be expanded again to distract the filler material within the cavity.

In one embodiment, a method includes expanding an expandable member to move a tissue portion and form a cavity within an interior of a bone-related structure. At least a portion of the cavity is filled with a filler material while simultaneously withdrawing a medium from the expandable member at a predefined ratio such that the tissue portion substantially maintains its moved position.

In another embodiment, an apparatus includes an expandable member having a collapsed configuration and an expanded configuration. The expandable member defines a first lumen in fluid communication with an interior of the expandable member, and a second lumen in fluid communication with an opening defined by the expandable member. The second lumen is configured to communicate a filler material through the opening and into an interior cavity of a bone-related structure when the expandable member is in an expanded configuration and disposed within the interior cavity of the bone-related structure.

In another embodiment, an apparatus includes an elongate body that defines a first lumen and a second lumen and an expandable member coupled to a distal end portion of the elongate body. The first lumen is in fluid communication with an interior volume of the expandable member. The elongate body also defines an opening that is in fluid communication with the second lumen. The opening of the elongate body is disposed proximally to a longitudinal mid-point of the expandable member. The second lumen is configured to deliver a filler material through the opening and into an interior cavity within a bone-related structure while the expandable member is in an expanded configuration and disposed within the interior cavity within the bone-related structure.

It is noted that, as used in this written description and the appended claims, the singular forms "a," "an" and "the" include plural referents unless the context clearly dictates otherwise. Thus, for example, the term "a lumen" is intended to mean a single lumen or a combination of lumens. Furthermore, the words "proximal" and "distal" refer to direction closer to and away from, respectively, an operator (e.g., surgeon, physician, nurse, technician, etc.) who would insert the medical device into the patient, with the tip-end (i.e., distal end) of the device inserted inside a patient's body. Thus, for example, the catheter end inserted inside a patient's body would be the distal end of the catheter, while the catheter end outside a patient's body would be the proximal end of the catheter.

The term "tissue" is used here to mean an aggregation of similarly specialized cells that are united in the performance of a particular function. For example, a tissue can be a soft tissue area (e.g., a muscle, connective tissue, ligaments), a hard tissue area (e.g., a bone structure), a vertebra, an intervertebral disc, a tumor, etc.

The term "bone-related structure" is used here to mean any anatomical structure associated with a hard or soft tissue, including, for example, a hard-tissue component of the spine such as a vertebra or a soft-tissue component of the spine such as an intervertebral disc.

The term "cannula" is used here to mean a component of an apparatus having one or more passageways configured to receive a device or other component. A cannula can be used to provide percutaneous access to an area within a patient's body. For example, a cannula can be substantially tubular. A cannula can have one or more of a variety of different shapes and size, such as having a round or octagonal outer perimeter.

FIG. 1 is a schematic illustration of an example of a medical device that can be used to perform the methods described herein. A medical device 10 can be used, for example, to perform minimally-invasive surgical procedures such as a percutaneous medical procedure within, or near, a bone-related structure. The medical device 10 includes an expandable member 28 that can be moved from a collapsed configuration to an expanded configuration to move or distract a tissue portion within a bone-related structure B, such as a vertebra or intervertebral disc. For example, the medical device 10 can be inserted into a bone-related structure with the expandable member 28 in the collapsed configuration. The expandable member 28 can then be moved to the expanded configuration while disposed within the bone-related structure. The medical device 10 can also be used to deliver a filler material 30 into a cavity or void formed within the bone-related structure B, while substantially maintaining the moved or distracted position of the tissue portion. The medical device 10 includes an elongate body 20 having a distal end portion 22 and a proximal end portion 24. In some embodiments, the expandable member 28 is coupled to the elongate body 20. In other embodiments, the elongate body 20 is formed of an expandable material and is monolithically formed with an expandable member 28.

Specifically, in one embodiment, the elongate body 20 defines a first lumen (not shown in FIG. 1) and a second lumen (not shown in FIG. 1) that extend through the elongate body 20. An expandable member 28 is coupled to the distal end portion 22 of the elongate body 20. The expandable member 28 defines an interior volume, and the first lumen is in fluid communication with the interior volume of the expandable member 28. The expandable member 28 can be moved between an expanded configuration and a collapsed configuration, and various partially expanded and collapsed configurations. For example, the first lumen can be coupled to a device 40 that can deliver an inflation medium, such as a fluid, to the first lumen. The first lumen can optionally also be coupled to a suction source 42 that can be used to remove the inflation medium from the interior volume of the expandable member 28 to deflate or partially deflate the expandable member 28. In some embodiments, the expandable member 28 can be deflated without the use of a suction source. For example, pressure can be exerted on an exterior of the expandable member 28 (e.g., from a filler material being disposed around the exterior of the expandable member) and force the inflation medium out of the expandable member 28. In other embodiments, the expandable member 28 may be sufficiently elastic such that the expandable member 28 automatically deflates as the inflation source is deactivated. The interior volume within the expandable member 28 is greater when the expandable member is in the expanded configuration than when the expandable member 28 is in the collapsed configuration. The expandable member 28 in the expanded configuration can distract or move the tissue portion within the bone-related structure B.

The second lumen can be in fluid communication with one or more openings (not shown in FIG. 1) defined by the elongate body 20 and/or defined by the expandable member 28. A device 44 can be coupled to the second lumen to provide the filler material 30, such as bone cement, to the second lumen. The second lumen can communicate the filler material 30 to an interior of a bone-related structure B as described in more detail below. The devices 40, 42 and 44 can be separate components or combined into a single device, such as a syringe, that can provide the inflation medium and the filler material to the medical device 10, and also provide a suction source to remove the inflation medium.

In some embodiments, the first lumen and the second lumen share a common axis (i.e., co-axial). For example, the second lumen can extend through a center of the expandable member 28 such that the first lumen surrounds the second lumen, or the second lumen can be outside of the expandable member 28 and surrounding the first lumen. Alternatively, the first lumen and the second lumen can be offset from each other. For example the first lumen and the second lumen can extend parallel to each other, but not co-axially (see, e.g., FIG. 11).

In some embodiments, the elongate body 20 is formed with an expandable material and defines the first lumen and the second lumen. In such an embodiment, a portion (e.g., a distal portion) of the elongate body 20 defines the expandable member 28. The expandable member 28 can define one or more openings in fluid communication with the second lumen through which the filler material 30 can be communicated and into the interior of the bone-related structure B.

In some embodiments, the medical device 10 is used in combination with an access cannula 26. In use, the medical device 10 can be percutaneously inserted into a bone-related structure via, for example, the access cannula 26. For example, in one use, a distal end of the access cannula 26 is inserted through a wall of the bone-related structure B. The medical device 10 is moved through a lumen of the access cannula with the expandable member 28 in the collapsed configuration. The expandable member 28 can be positioned outside of the access cannula 26 and disposed within an interior of the bone-related structure B. The expandable member 28 can then be moved to the expanded configuration by filling the interior volume with an inflation medium. The expansion of the expandable member 28 can move or distract tissue within the interior of the bone-related structure B forming a cavity or void within the bone-related structure B.

After distracting or moving the tissue portion, the filler material 30 can be delivered to the cavity within the bone-related structure B. For example, in some embodiments, the expandable member 28 can be partially deflated or moved to a partially expanded configuration prior to, or simultaneously with, the delivering of the filler material 30 into the cavity. In some embodiments, during the filling of the filler material 30, the elongate body 20 can also be moved proximally while simultaneously deflating the expandable member, such that a portion of the expandable member 28 is removed from the cavity. In some embodiments, the expandable member 28 is sufficiently flexible or elastic, such that as the filler material 30 is being delivered into the cavity of the bone-related structure B, the expandable member 28 is compressed by the filler material 30, disposing the filler material 30 around an exterior of the expandable member 28.

After the filler material 30 has been delivered into the cavity of the bone-related structure B, the expandable member 28 can optionally be expanded or moved to a second expanded configuration. The expansion of the expandable member 28 after the filler material 30 has been delivered can move the filler material 30 such that at least a portion of the filler material 30 is in contact with the distracted tissue portion of the bone-related structure B. Such movement or compression of the filler material 30 can form an egg-shell type arrangement of the filler material 30 around the outer boundary of the cavity of the bone-related structure B. After the movement of the filler material 30, the expandable member 28 can be can be moved to the collapsed configuration and removed from the cavity.

Having described above various general examples, several examples of specific embodiments are now described. These embodiments are only examples, and many other configurations of a medical device 10 are contemplated FIGS. 2 and 3 illustrate a medical device according to an embodiment of the invention. FIG. 2 is a side view of a portion of a medical device 110 in a collapsed configuration and partially disposed within, and extending from, an access cannula 126. The medical device 110 includes an elongate body 120 having a distal end portion 122 and a proximal end portion (not shown in FIG. 2). An expandable member 128 is coupled to the distal end portion 122 of the elongate body 120. The expandable member 128 can be coupled to the elongate body 120, for example, with an adhesive, a heat seal, a laser bond, a radio-frequency (RF) weld, or other suitable coupling means. The expandable member 128 can be moved between the collapsed configuration, as shown in FIG. 2 and an expanded configuration as shown in FIG. 3.

As shown in the cross-sectional of FIG. 3, the elongate body 120 defines a first lumen 132 and a second lumen 134. In this embodiment, the first lumen 132 and the second lumen 134 share a common longitudinal axis A defined by the elongate body 120. The first lumen 132 is in fluid communication with an interior volume 136 defined by the expandable member 128. An inflation medium can be delivered into the interior volume 136 of the expandable member 128 to move the expandable member 128 from the collapsed configuration to the expanded configuration. The second lumen 134 is in fluid communication with an opening 138 defined at a distal end of the elongate body 120. The second lumen 134 can be used to communicate or deliver a filler material 130 to an interior of a bone-related structure, such as a vertebra or intervertebral disc. An annular seal member 146 can also be coupled to the elongate body 120 to help prevent filler material from entering into a lumen 148 of the access cannula 126 after being delivered through the opening 138. Note that the size of the lumen 148 is exaggerated for purposes of illustration and actually can have a much smaller size associated with the manufacturing tolerances of the elongate body 120 and access cannula 126. An example use of the medical device 130 is described below with reference to FIGS. 5-8.

Figure 4:
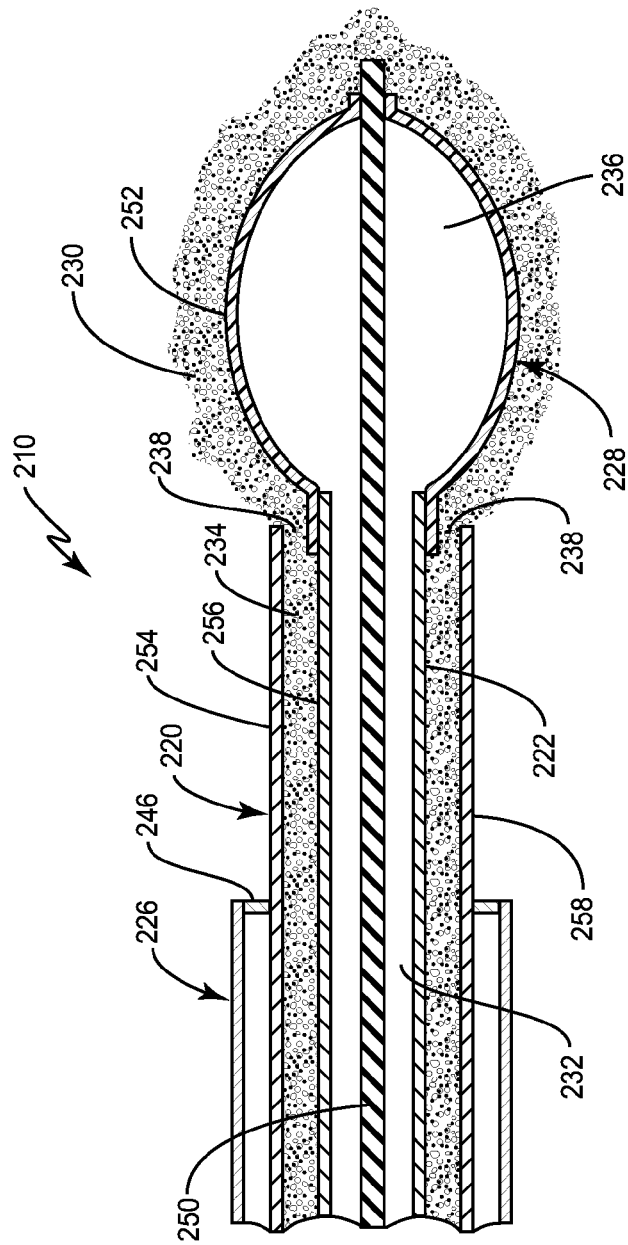
FIG. 4 is a side cross-sectional view of a portion of another embodiment of a medical device disposed partially within, an extending from, a portion of an access cannula.

FIG. 4 is a cross-sectional view of an embodiment of a medical device 210 shown partially disposed within an access cannula 226. The medical device 210 is similar to the medical device 110 and can be used in a similar manner. In this embodiment, the medical device 210 includes an elongate body 220 and an expandable member 228. The elongate body 210 includes an outer wall member 254 and an inner wall member 256. The expandable member 228 is coupled to a distal end portion 222 of the inner wall member 256 of the elongate body 220. The inner wall member 256 and the outer wall member 254 can be formed monolithically or as separate components. The expandable member 228 is shown in an expanded configuration in FIG. 4, but can be moved between a collapsed configuration (not shown) and the expanded configuration as with the previous embodiments. In this embodiment, the medical device 220 also includes a rod 250 coupled at a distal end to the expandable member 228. The rod 250 is used to help guide and/or to support the expandable member 228. The medical device 210 also includes a seal member 246 that performs the same function as the seal member 146 described in the previous embodiment.

The inner wall member 256 of the elongate body 220 defines a first lumen 232 in fluid communication with an interior volume 236 of the expandable member 228, and the outer wall member 254 and inner wall member 256 collectively define a second lumen 234 in fluid communication with an opening 238. As shown in FIG. 4, in this embodiment, the opening 238 is at a distal end of the outer wall member 254, which is disposed proximal of a longitudinal mid-point 252 of the expandable member 228. In this embodiment, the second lumen 234 surrounds the first lumen 232 and each of the first lumen 232 and the second lumen 234 have an annular cross-section. In other embodiments, the second lumen 234 does not surround the first lumen 232. For example, in some embodiments, the second lumen does not have an annular cross-section and is positioned parallel with the first lumen and in a cross-sectional view is only on one side of the first lumen (see, e.g., FIG. 11). In some embodiments, neither of the first lumen 232 or the second lumen 234 have an annular cross-section. As described for the previous embodiments, the second lumen 234 can be used to deliver a filler material 230 to an interior cavity or void within a bone-related structure (not shown).

In some embodiments, the rod 250 can define an interior lumen. In such an embodiment, the lumen of the rod 250 can be in fluid communication with an opening on a distal end, similar to the opening 138 of the medical device 110. The lumen of the rod 250 can be used in addition to the second lumen 134 to communicate the filler material 130 to the interior cavity of a bone-related structure.

Figure 7:
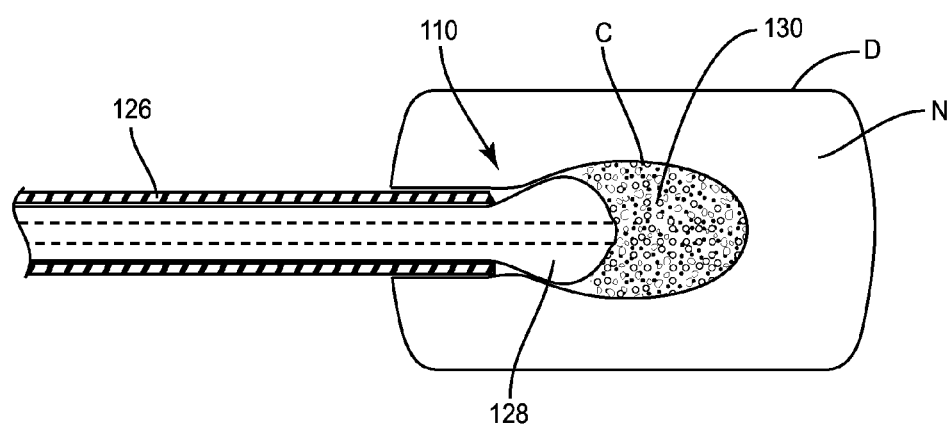
FIG. 7 is a side view of the medical device of FIG. 5 shown in a partially expanded configuration and within a cross-sectional view of a portion of an access cannula and partially withdrawn from a cross-sectional view of an intervertebral disc.
Figure 8:
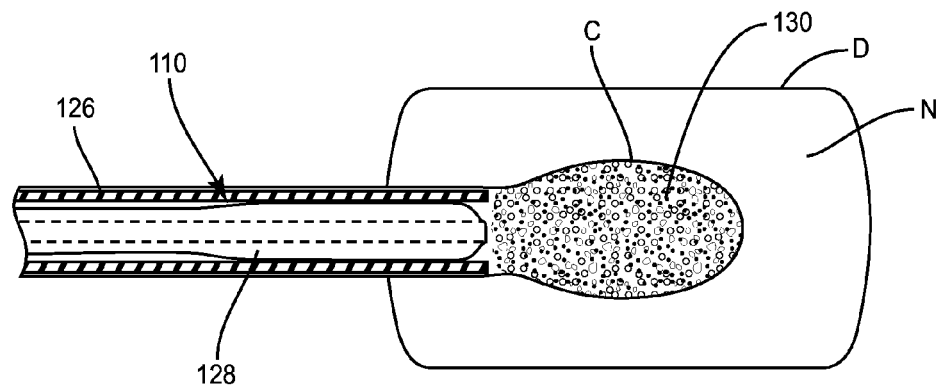
FIG. 8 is a side view of the medical device of FIG. 5 shown in a collapsed configuration and within a cross-sectional view of a portion of an access cannula and withdrawn from a cross-sectional view of an intervertebral disc.
Figure 9:
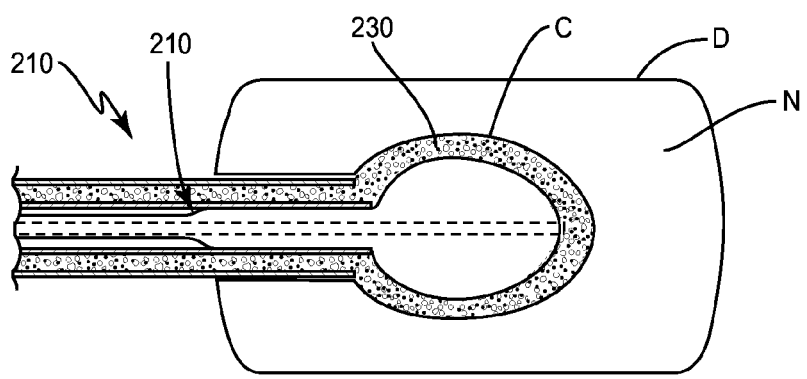
FIG. 9 is a side view of a portion of medical device according to another embodiment shown in a partially expanded configuration and within a cross-sectional view of another portion of the medical device and a cross-sectional view of an intervertebral disc.

The medical device 110 and the medical device 210 can each be used in a similar manner to treat a bone-related structure, such as a vertebra or intervertebral disc. FIGS. 5-8 illustrate the use of the medical device 110 to treat an intervertebral disc, and FIG. 9 illustrates the use of the medical device 210 to treat an intervertebral disc. That said, medical device 210 and medical device 110 can each be used alternatively to treat a vertebra.

Figure 5:
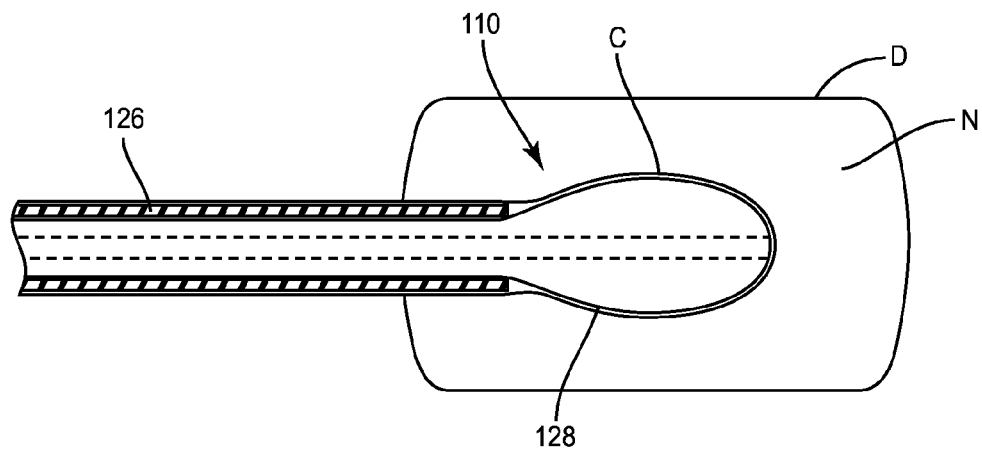
FIG. 5 is a side view of a portion of an embodiment of a medical device shown in an expanded configuration and within a cross-sectional view of a portion of an access cannula and a cross-sectional view of an intervertebral disc.

As described previously, the medical device 110 can be percutaneously inserted into an interior of an intervertebral disc D via an access cannula 126. For example, the medical device 110 can be inserted through a lumen of the access cannula with the expandable member 128 in a collapsed configuration. After being disposed within the interior of the intervertebral disc D, the expandable member 128 can be moved to an expanded configuration as shown in FIG. 5. In the expanded configuration, the expandable member 128 can move a portion of the nucleus pulposus N (also referred to as "tissue portion") within the interior of the disc D. This process will form a cavity or void C within the disc D that is at the time of expanding substantially filled with the expandable member 128.

Figure 6:
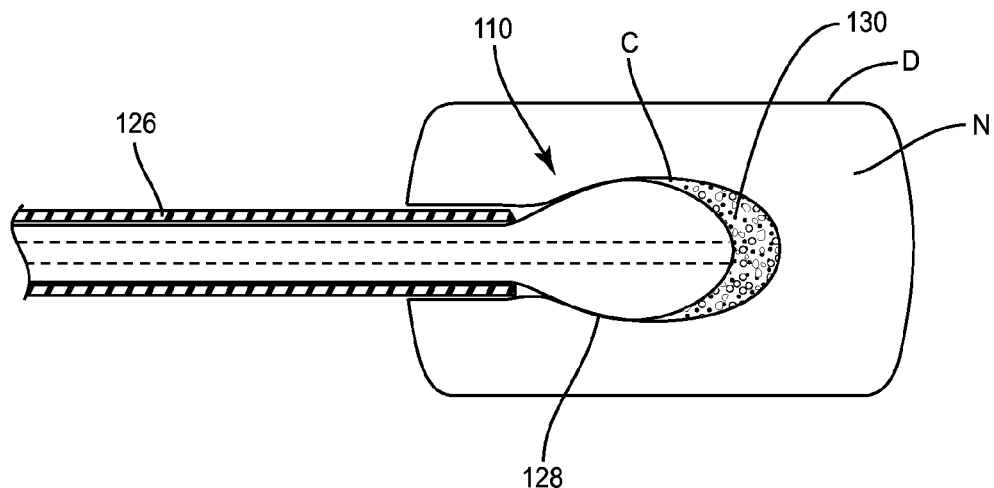
FIG. 6 is a side view of the medical device of FIG. 5 shown in a partially expanded configuration and within a cross-sectional view of a portion of an access cannula and partially withdrawn from a cross-sectional view of an intervertebral disc.

The expandable member 128 can then be partially deflated or moved to a partially expanded configuration during substantially the same time period as a filler material 130 is being delivered into the cavity C, as shown in FIG. 6. This allows the moved tissue portion within the disc D to substantially maintain the moved position while the filler material 130 is being delivered into the cavity C. In addition, the medical device 110 can be pulled proximally during the filling of the filler material 130 and during the deflating of the expandable member 128 such that a portion of the expandable member 128 is removed from the cavity C and disposed within a lumen of the access cannula 126 as shown in FIG. 6.

In some embodiments, removal of the expandable member 128 and delivering of the filler material 130 can be a 1:1 exchange within the cavity of the disc D. For example, after formation of cavity C, the amount of volume reduced within the expandable member 128 is equivalent to or substantially the same as the increase in volume of filler material 130 within the cavity C. In other embodiments, the medical device 110 can be configured to exchange the volume of the expandable member 128 with the filler material 130 at different rates of exchange for example, a ratio of 1:1.1, 1:1.3, etc. The progression of the exchange of the expandable member 128 with the filler material 130 within the cavity C is illustrated in FIGS. 7 and 8. FIG. 7 illustrates the expandable member 128 partially collapsed/expanded and partially removed from the cavity C. FIG. 8 illustrates the expandable member in a collapsed configuration and disposed within the lumen of the access cannula 126, and the cavity C substantially filled with filler material 130.

FIG. 9 illustrates the medical device 210 in a partially expanded configuration and disposed within nucleus pulposus N of an intervertebral disc D. The medical device 210 can be used in the same manner as described above for medical device 110. FIG. 9 illustrates the filler material 230 being delivered to an interior cavity C such that the filler material 230 substantially surrounds the expandable member 228. FIG. 9 also illustrates the use of the medical device 210 without the use of an access cannula.

Although not shown in the figures, the expandable members 128 and 228 of the medical device 110 and the medical device 210, respectively, can be expanded within an intervertebral disc such that an endplate of a superior vertebra and/or an endplate of an inferior vertebra are moved, expanding the space between the superior and inferior endplates (e.g., distracting the endplates). The expandable members 128 and 228 can also be expanded to laterally move or distract annular walls of the intervertebral disc (e.g., the annulus fibrosis).

Figure 10:
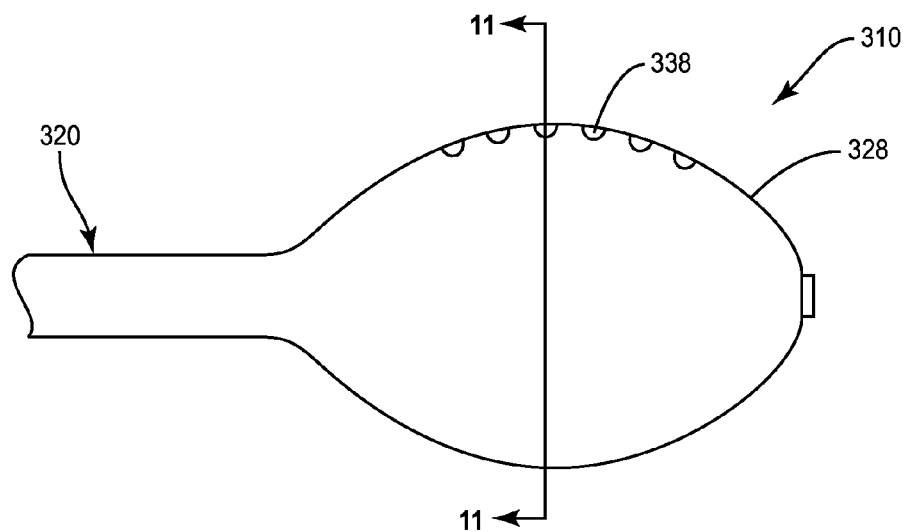
FIG. 10 is a side view of a portion of a medical device according to another embodiment.
Figure 11:
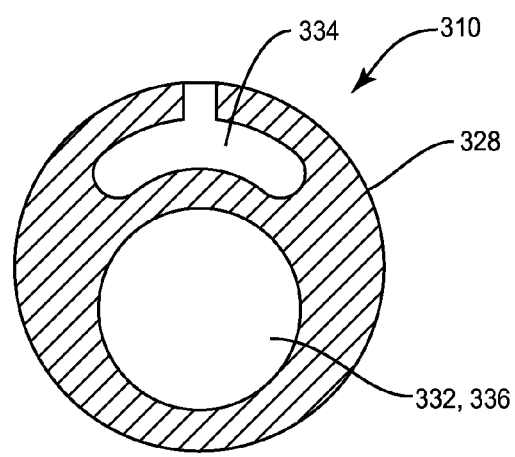
FIG. 11 is a cross-sectional view of the medical device of FIG. 10 taken along line 11-11 in FIG. 10.

FIGS. 10 and 11 illustrate a portion of a medical device 310 according to another embodiment, and FIGS. 12-15 illustrate an example of a use of the medical device 310 within a vertebra. The medical device 310 includes an elongate body 320 that is formed at least partially with an expandable material. For example, the elongate body 320 can be formed entirely with an expandable material. In other embodiments, only a portion of the elongate body 320 is formed with an expandable material. The elongate body 320 includes an expandable portion 328 that defines an interior volume 336 and has a range of motion between a collapsed configuration and an expanded configuration as described above for previous embodiments of an expandable member.

The elongate body 320 also defines a first lumen 332 and a second lumen 334 that extend within the expandable portion 328, as shown in the cross-sectional view of FIG. 11. The first lumen 332 is in fluid communication with the interior volume 336 defined by the expandable portion 328 and can be used to inflate and deflate the expandable portion 328 with an inflation medium as previously described. The second lumen 334 is in fluid communication with multiple openings 338 defined by the expandable portion 328. Although five openings 338 are shown, in other embodiments the expandable portion 328 may have more or less openings 338. The second lumen 334 can deliver a filler material to an interior region of a bone-related structure as previously described via the openings 338. The medical device 310 can be movably disposed within an access cannula to assist in percutaneous entry into a bone-related structure.

Figure 12:
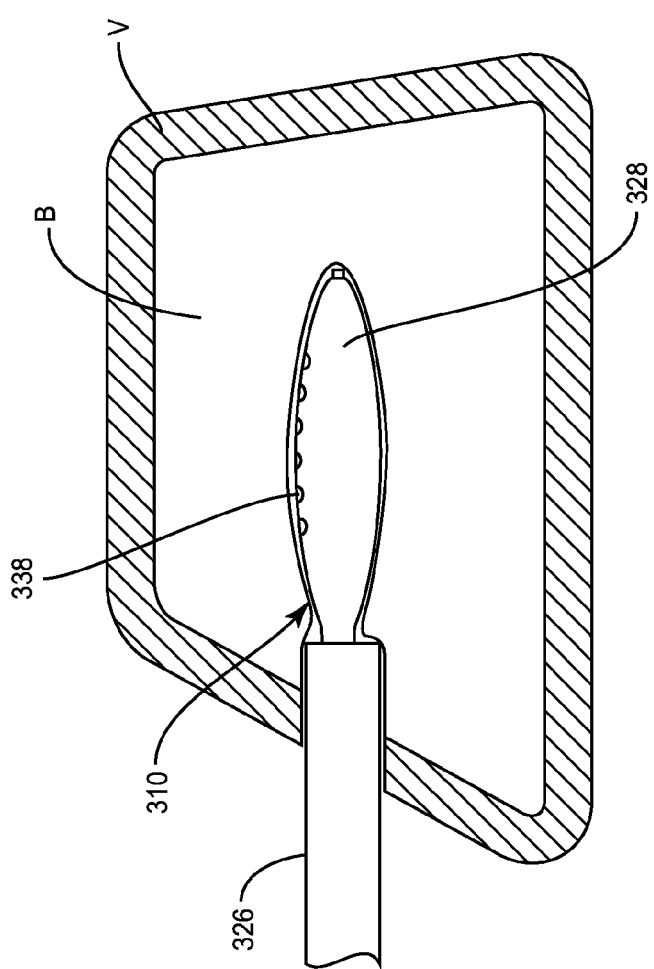
FIG. 12 is a side view of a portion of the medical device of FIG. 10 shown in a collapsed configuration and within a cross-sectional view of a vertebra.
Figure 13:
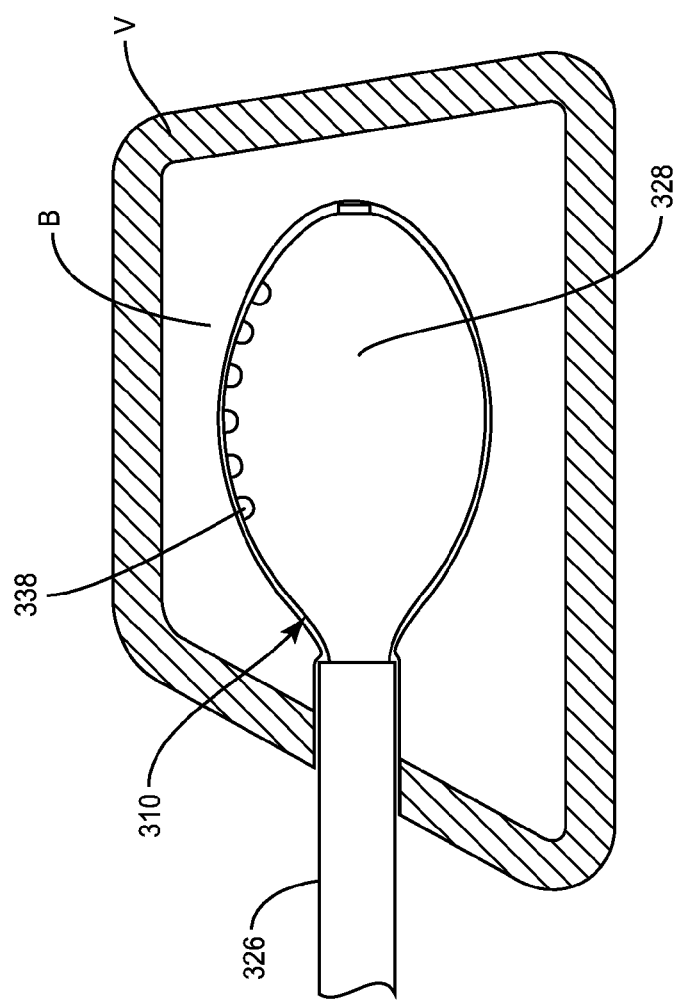
FIG. 13 is a side view of a portion of the medical device of FIG. 10 shown in an expanded configuration and within a cross-sectional view of a vertebra.
Figure 14:
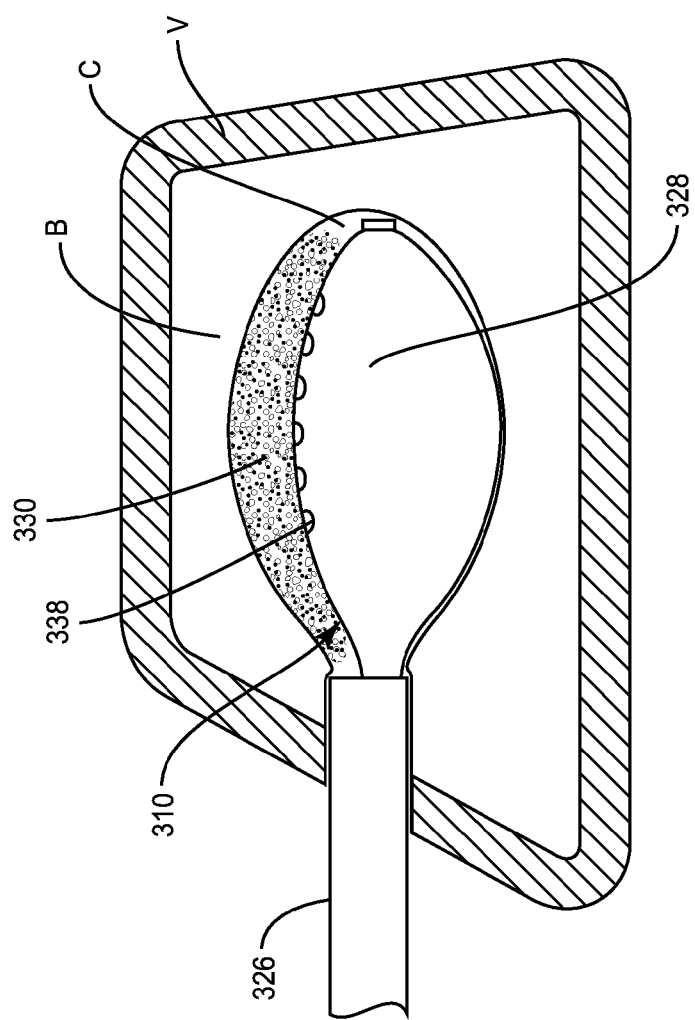
FIG. 14 is a side view of a portion of the medical device of FIG. 10 shown in a partially expanded configuration and within a cross-sectional view of a vertebra.
Figure 15:
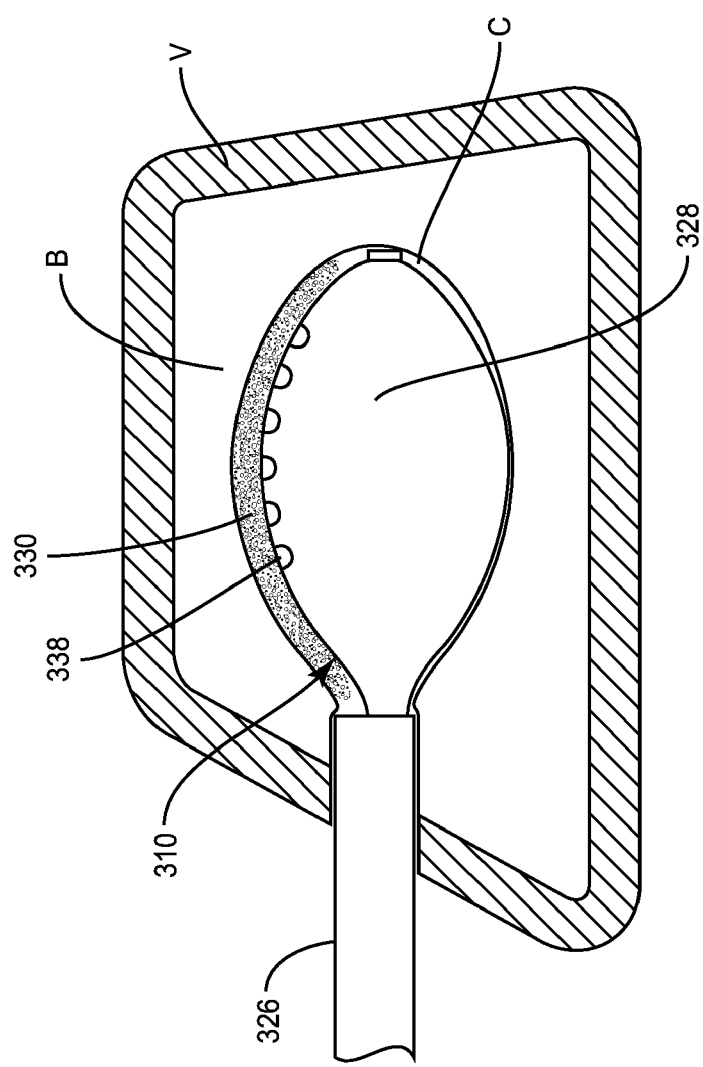
FIG. 15 is a side view of a portion of the medical device of FIG. 10 shown in an expanded configuration and within a cross-sectional view of a vertebra.

As shown in FIG. 12, the medical device 310 can be partially inserted into an interior of a vertebra V with the expandable portion 328 in a collapsed configuration via an access cannula 326. As shown in FIG. 13, the expandable portion 328 can be moved to an expanded configuration to move or distract cancellous bone B within the vertebra V, forming a cavity C. As with the previous embodiments, the expandable portion 328 can be partially deflated at substantially the same time, or during a portion of the time period, as a filler material 330 is being delivered through the second lumen 334 and into the cavity C, as shown in FIG. 14. After the filler material 330 is deposited within the cavity C, the expandable portion 328 can be expanded again to a second expanded configuration to move or compress the filler material 330 around the outer boundary of the cavity C, as shown in FIG. 15. After moving or compressing the filler material 330, the expandable portion 328 can be moved to a collapsed configuration and removed from the cavity C. Although, the medical device 310 was shown being used within a vertebra, the medical device 310 can also be used in an intervertebral disc or other bone-related structures.

Figure 16:
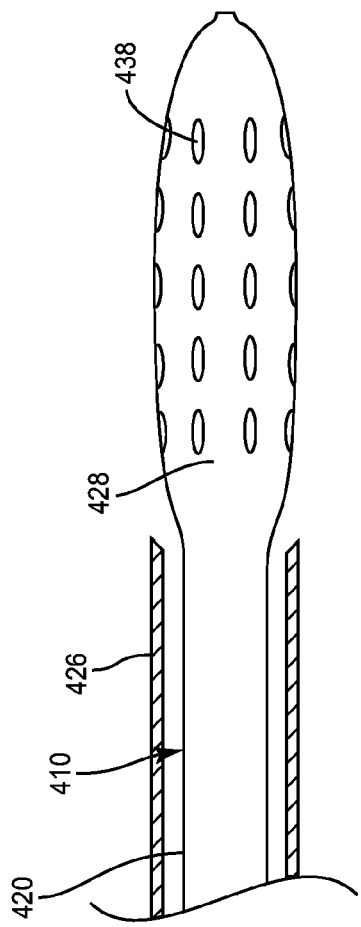
FIG. 16 is a side view of a portion of a medical device according to another embodiment shown in a collapsed configuration.
Figure 17:
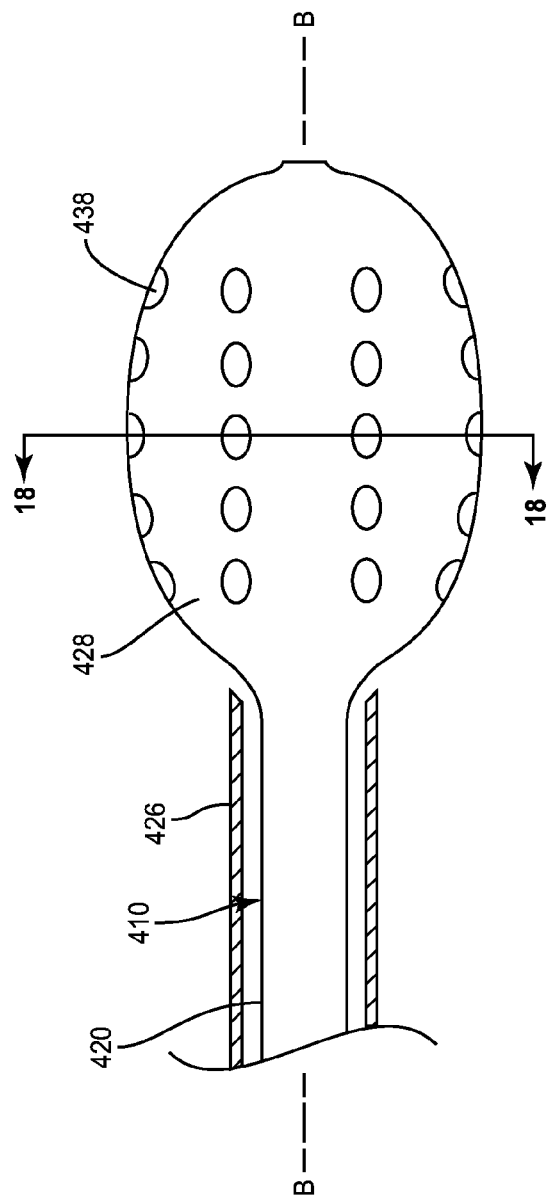
FIG. 17 is a side view of the portion of the medical device of FIG. 16 shown in an expanded configuration.
Figure 18:
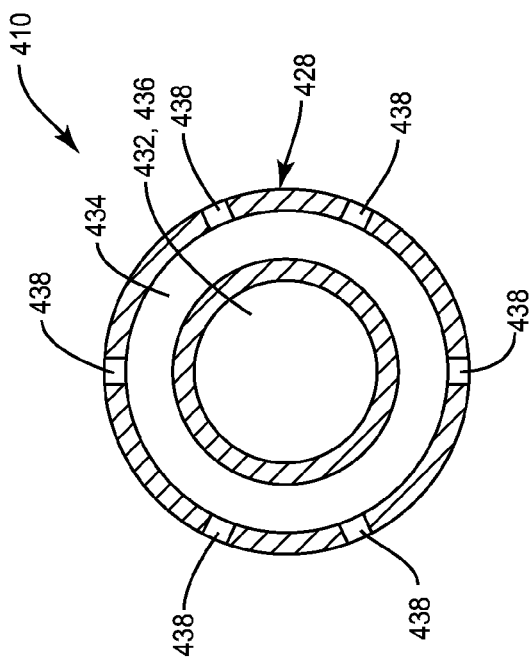
FIG. 18 is a cross-sectional view of the portion of the medical device of FIGS. 16 and 17 taken along line 18-18 in FIG. 17.

FIGS. 16-18 illustrate a medical device according to yet another embodiment. A medical device 410 is similar to the medical device 310 and can be used in a similar manner. The medical device 410 includes an elongate body 420 at least partially formed with an expandable material. The elongate body 420 includes an expandable portion 428 disposed at a distal end portion of the elongate body 420 that defines a volume 436 and has a range of motion between a collapsed configuration and an expanded configuration. FIG. 16 illustrates the expandable portion 428 in a collapsed configuration; FIGS. 17 and 18 illustrate the expandable portion 428 in an expanded configuration. The medical device 410 can be used with an access cannula 426 as shown in FIGS. 16 and 17 to percutaneously access a bone-related structure.

As with the medical device 310, the elongate body 420 defines a first lumen 432 and a second lumen 434 each of which extend within the expandable portion 428. The elongate body 420 also defines a longitudinal axis B. The first lumen 432 is in fluid communication with the interior volume 436 and can be used to communicate an inflation medium to and from the interior volume 436. The second lumen 434 is in fluid communication with multiple openings 438 defined by the expandable portion 428 and can be used to communicate a filler material through the openings 438 and into an interior of a bone-related structure. As shown in FIG. 18, in this embodiment, the first lumen 432 and the second lumen 434 have the same longitudinal axis B defined by the elongate body 420 (i.e., are co-axial). The medical device 410 can optionally include an elongate rod (not shown) or other component coupled to the elongate body 410 to provide support and/or to guide the elongate body 420 as the medical device 410 is being maneuvered within a bone-related structure. For example an elongate rod can be disposed through a center of the first lumen 432 and coupled to the elongate body 420. The medical device 310 can also optionally include an elongate rod.

Figure 19:
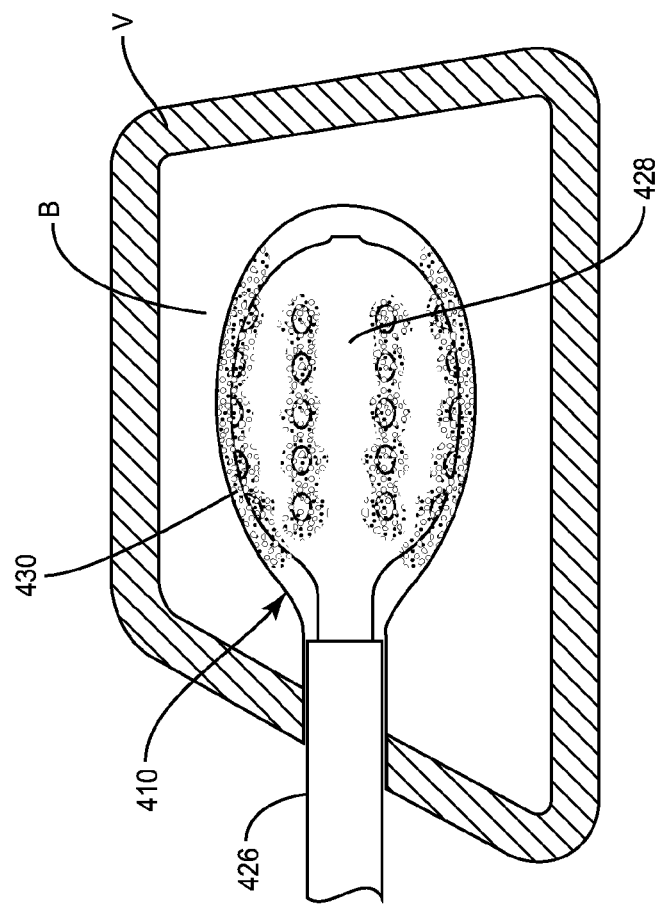
FIG. 19 is a side view of the portion of the medical device of FIG. 16 shown in an expanded configuration and within a cross-sectional view of a vertebra.

FIG. 19 illustrates an example of the medical device 410 in use within a vertebra V The medical device 410 can be used in the same manner as the previous embodiment to form a cavity within the cancellous bone B of the vertebra V and then fill the cavity C with a filler material 430. In some embodiments, the medical device 410 only includes openings 438 on a top side, a bottom side and/or a middle portion of the expandable member 428. Thus, the expandable member 428, as well as the expandable member 328, can include one or more openings in a variety of different locations and/or patterns and configurations. The openings can also be a variety of different shapes and/or sizes.

FIGS. 20-22 illustrate an embodiment of a medical device 510 shown in a collapsed configuration. The medical device 510 is similar to the medical device 310 and the medical device 410 and can be used to treat a bone-related structure in a similar manner. The medical device 510 includes an elongate body 520 and an expandable member 528 coupled to the elongate body 520. In this embodiment, the elongate body 520 defines a first lumen 532 and a second lumen 534, and the expandable member 528 defines a first lumen 532' and a second lumen 534' that correspond to the first lumen 532 and second lumen 534 of the elongate body 520. Thus, the lumens of the expandable member 528 and elongate body 520 combined form a continuous first lumen and a continuous second lumen.

The first lumen 532' of the expandable member 528 defines an interior volume of the expandable member 528 The expandable member 528 has a range of motion between a collapsed configuration and an expanded configuration. The interior volume of the expandable member 528 when in the expanded configuration is greater than the interior volume of the expandable member 528 when in the collapsed configuration. The second lumen 534' of the expandable member 528 is in fluid communication with one or more openings 538 defined by the expandable member 528 and can communicate a filler material (not shown) through the openings 538 and into a cavity or void within a bone-related structure as previously described. The medical device 510 can be used in the same manner as the previous embodiments and can perform the same functions.

Figure 23:
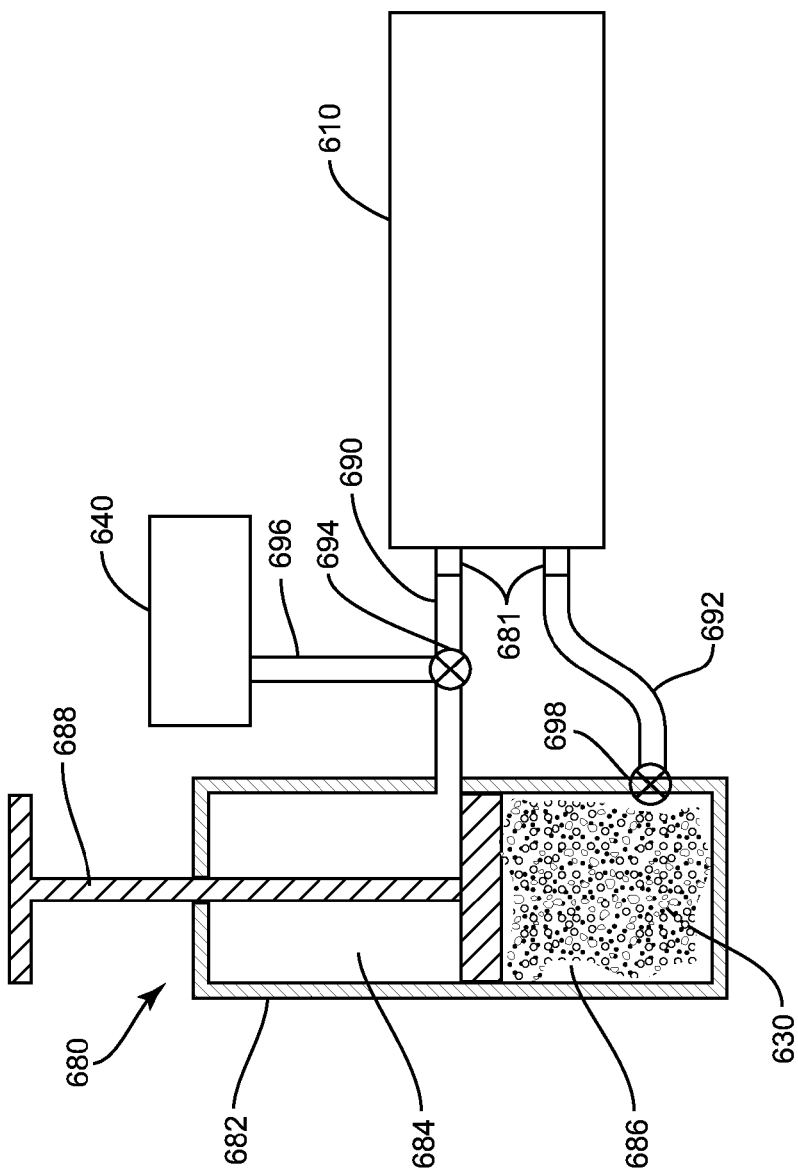
FIG. 23 is a side view shown partially in cross-section of a syringe device and a schematic illustration of a medical device.

FIGS. 23-29 illustrate example embodiments of different syringe devices that can be coupled to any of the medical devices described herein (e.g., 10, 110, 210, etc.). Other types of syringes and delivery devices can alternatively be used. FIG. 23 is a partial cross-sectional view of a device 680 coupled to a medical device 610 (shown in schematic). The device 680 includes an outer body 682 and an actuator 688. The outer body 682 and the actuator 688 collectively define an interior region 684 and an interior region 686. The interior regions 684 can receive and contain an inflation medium (e.g., water or saline). The interior region 686 can receive and contain a filler material 630, (e.g., a bone cement, a hydrogel, bone graph material). The syringe device 680 can be coupled to a medical device 610 via a first tubular member 690 and a second tubular member 692. A valve 694 can be coupled to the tubular member 690. A fluid source 640 (e.g., a source of inflation medium) can be coupled to valve 694 via a tubular fluid delivery member 696. The tubular members 690 and 692 can be coupled to the medical device 610 with a fitting 681, such as a luer fitting, or other suitable coupling mechanism.

The first valve 694 can be moved between a first configuration and a second configuration. In the first configuration, the first valve 694 allows an inflation medium to flow from the fluid source 640 to the medical device 610 via the tubular members 696 and 690, but prevents flow within the tubular member 690 between the first valve 694 and the syringe device 680. In the second configuration, the first valve 694 prevents the inflation medium from passing from tubular fluid delivery member 696 and into the tubular member 690, but allows the inflation medium to flow between the medical device 610 and the syringe device 680 via the tubular member 690. A second valve 698 can be coupled to outer body 682 and to the tubular member 692. The second valve 698 can be moved between an open configuration and a closed configuration.

The syringe device 680 can be used to remove an inflation medium from the medical device 610 and from an expandable member (not shown) of the medical device 610 while supplying the filler material 630 to the interior of a bone-related structure as described herein. With the syringe device 680 coupled to the medical device 610 as shown in FIG. 23, the valve 694 can be positioned in the first configuration to allow an inflation medium to flow from the fluid source 640 into the expandable member of the medical device 610. The first valve 694 can then be moved to the second configuration and the second valve 698 moved to the open configuration. The actuator 688 then can be moved or pushed inward into the outer body 682 such that the filler material 630 is moved from the interior region 686, into the medical device 610 and then into a cavity of a bone-related structure. As the actuator 688 is moved inward, at least a portion of the inflation medium is drawn from the expandable member of the medical device 610 and into the syringe device 680. In addition, as the filler material 630 enters the interior cavity of the bone-related structure, a pressure will be exerted on an exterior of the expandable member, which will assist in the movement of the inflation medium from the expandable member and into the syringe device 680. In some embodiments, as the actuator 688 is moved inward, a suction is formed within the interior region 684 of the syringe device 680 to help draw the inflation medium into the syringe device 680.

Figure 24:
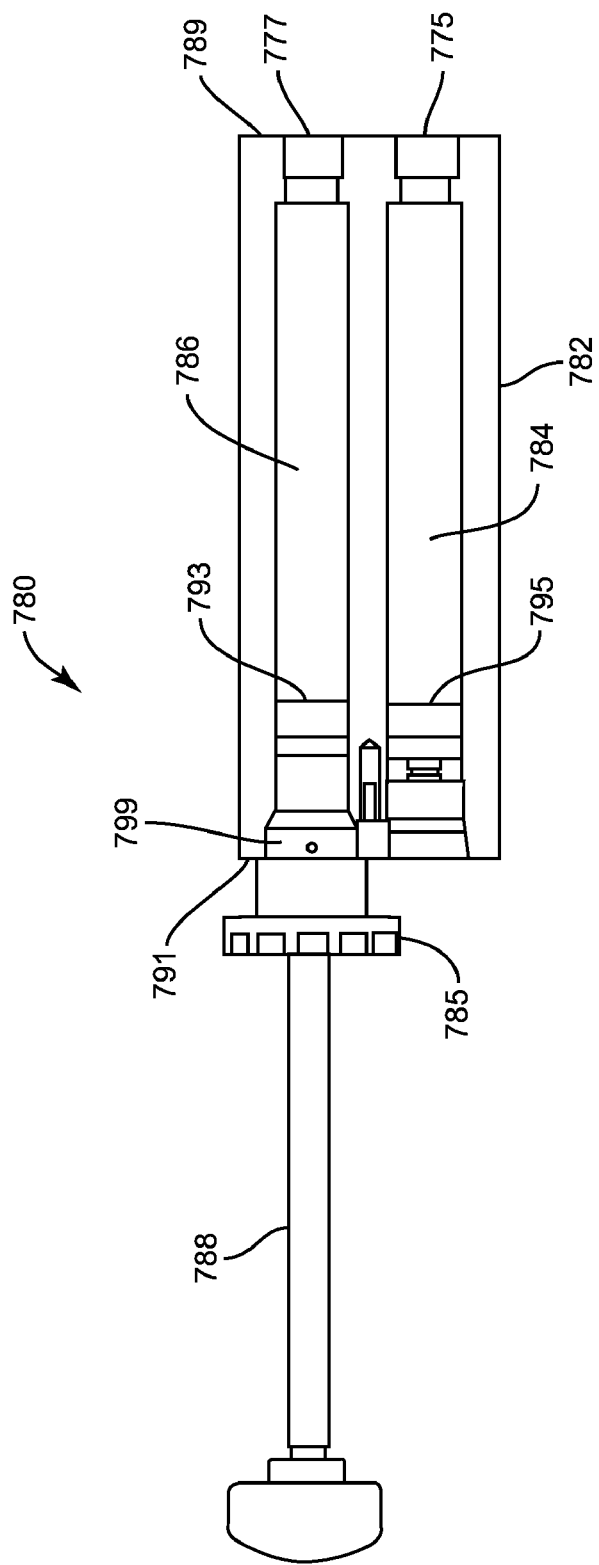
FIG. 24 is a side view of an embodiment of a syringe device.

FIG. 24 illustrates a syringe device 780 having an body member 782 that defines a first interior region or lumen 784 and a second interior region or lumen 786. The body member 782 also defines a first opening 777 in fluid communication with the first lumen 784 and a second opening 775 in fluid communication with the second lumen 786. A first plunger 793 is moveably disposed within the first lumen 786 and a second plunger 795 is movably disposed within the second lumen 784. An actuator 788 is coupled to a first end 791 of the body member 782. The actuator 788 can be releasably coupled to the body member 782 adjacent the first lumen 784 or the second lumen 786 with a quick-connect valve or fitting 799 as desired. For example, the actuator can be coupled to the body member 782 and engaged with the first plunger 793 and used to move the first plunger 793 proximally and distally within the first lumen 786. The actuator 788 can also be coupled to the body member 782 and engaged with the second plunger 795 and used to move the second plunger 795 proximally and distally within the second lumen 784.

A second end 789 of the body member 782 can be coupled to a proximal end of a medical device, such as those described herein (e.g., 10, 110, 210, 310, etc.) via, for example tubular members (not shown), as described in the previous embodiment. For example, a luer fitting (not shown) can be used to couple the syringe device 780 to one or more tubular members. The tubular members can also be coupled to the medical device in a similar manner.

In this embodiment, a filler material can be loaded into the first lumen 786 and the syringe device 780 can be coupled to a proximal end of a medical device as described above. With the actuator 788 coupled to the body member 782 and engaged with the first plunger 793 as shown in FIG. 24, the actuator 788 can be moved toward the distal end 789. This will cause the plunger 793 to move toward the distal end 789, pushing or moving the filler material out of the lumen 786 and into a cavity within a bone-related structure. As the actuator 788 and plunger 793 are moved toward the distal end 789, at least a portion of an inflation medium is drawn from an expandable member of the medical device coupled to the syringe device 780 and into the second lumen 784 of the syringe device 780. In addition, as the filler material enters the interior cavity of the bone-related structure, a pressure will be exerted on an exterior of the expandable member, which will assist in the movement of the inflation medium from the expandable member and into the lumen 784 of the syringe device 780.

In some embodiments, the second lumen 784 can be pre-filled with an inflation medium and the syringe device 780 can be used to fill or expand the expandable member of the medical device. Thus, in such an embodiment, both the filler material and the inflation medium can be pre-loaded into the syringe device 780. Alternatively, the filler material can be loaded into the syringe device 780 after expanding the expandable member. For example, the actuator 788 can first be coupled to the body member 782 such that it is engaged with the second plunger 795 and used to move the second plunger 795 distally within the second lumen 784 in a similar manner as described above for plunger 793. The plunger 795 can move the inflation medium out of the lumen 784 and into the expandable member. The actuator 788 can then be disengaged with the second plunger and moved to engagement with the first plunger 793 as previously described and shown in FIG. 24. The above procedure for moving the filler material and receiving the inflation medium as described above can then be performed.

Figure 25:
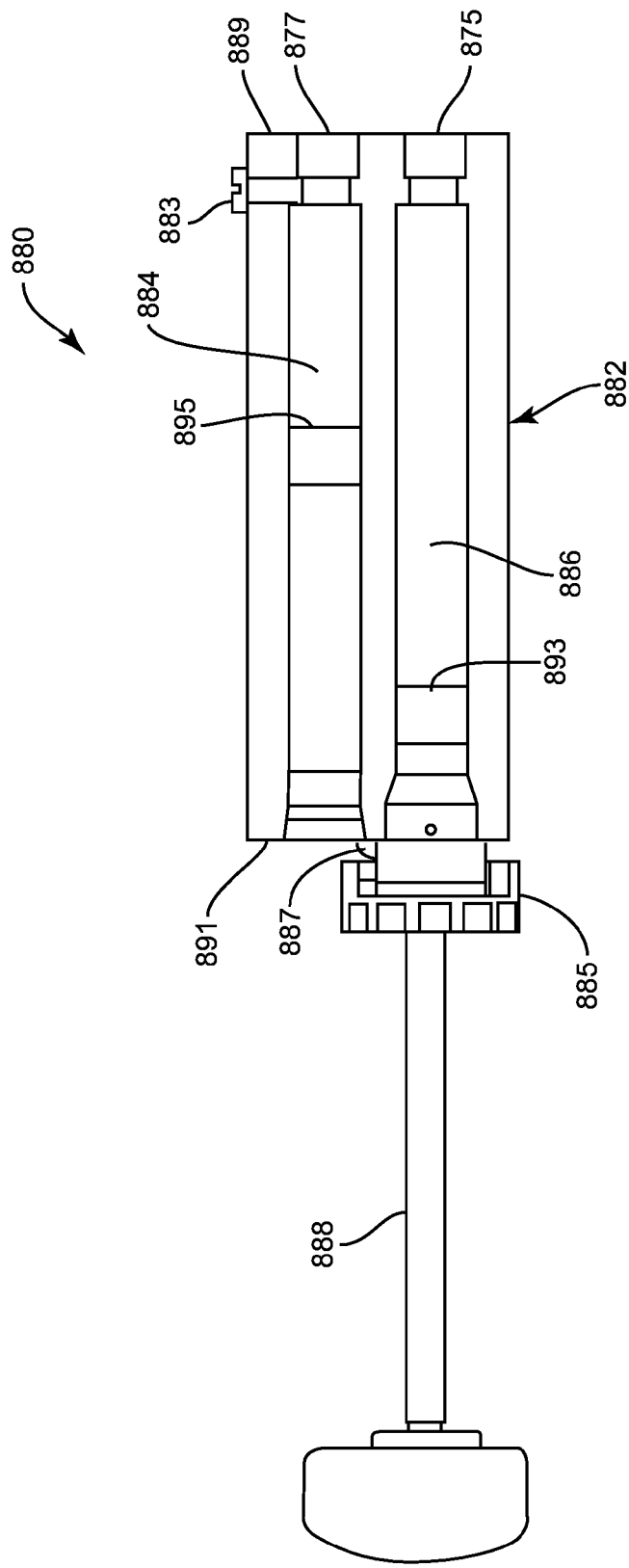
FIG. 25 is a side view of an embodiment of a syringe device in a first position.
Figure 26:
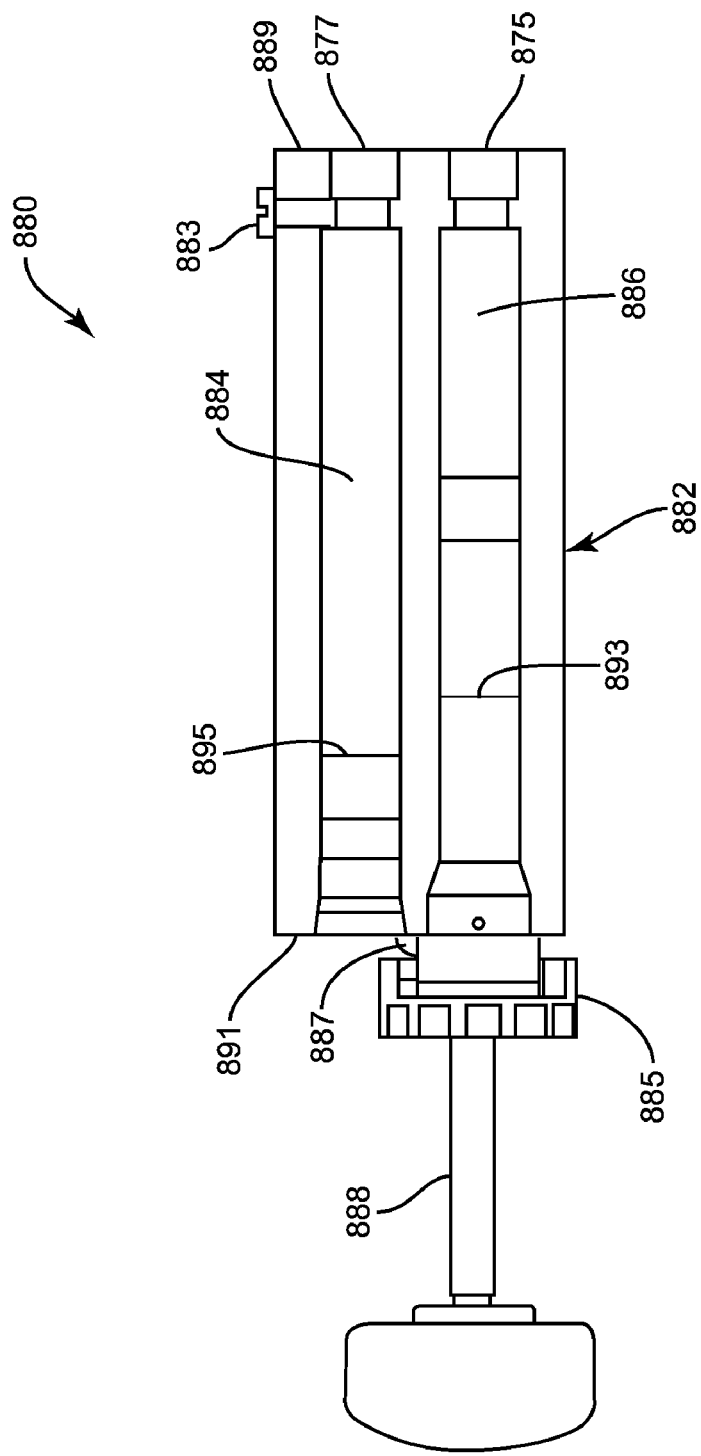
FIG. 26 is a side view of the syringe device of FIG. 25 in a second position.
Figure 27:
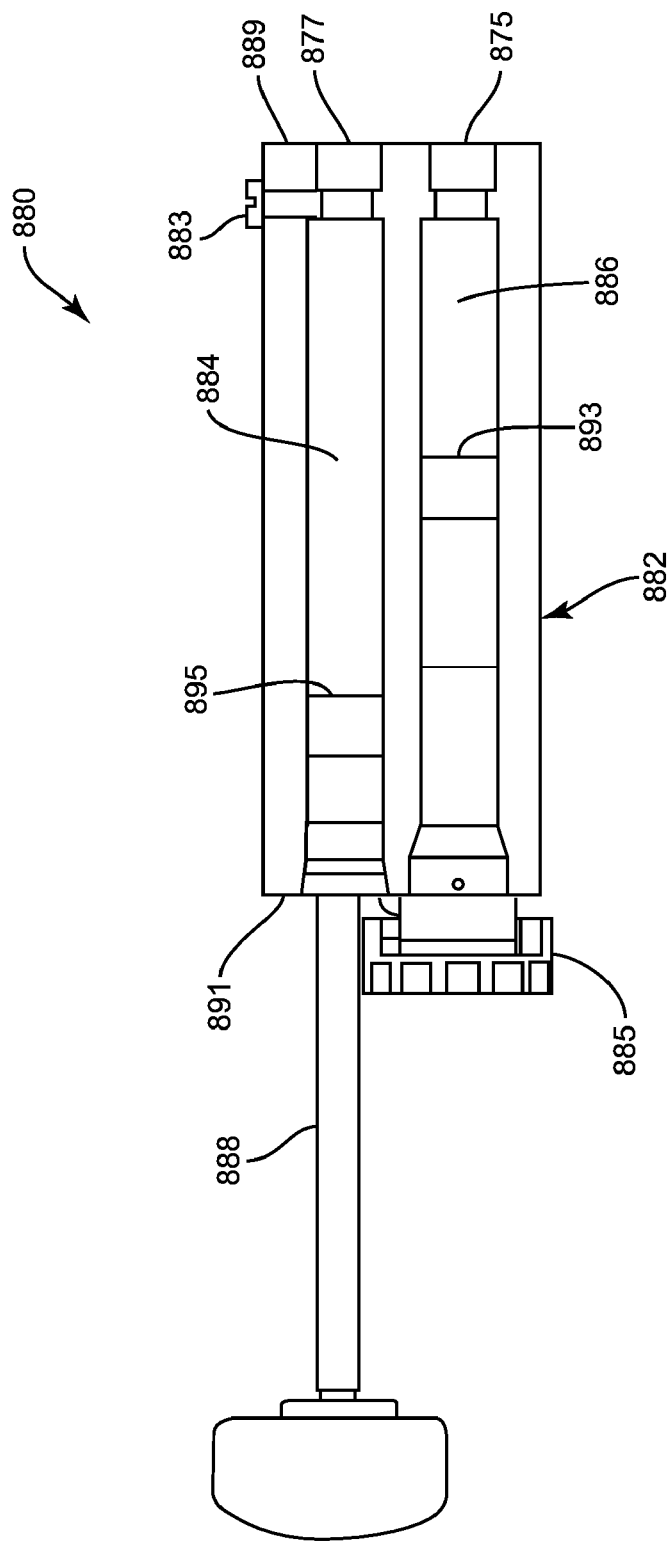
FIG. 27 is a side view of the syringe device of FIG. 25 in a third position.
Figure 28:
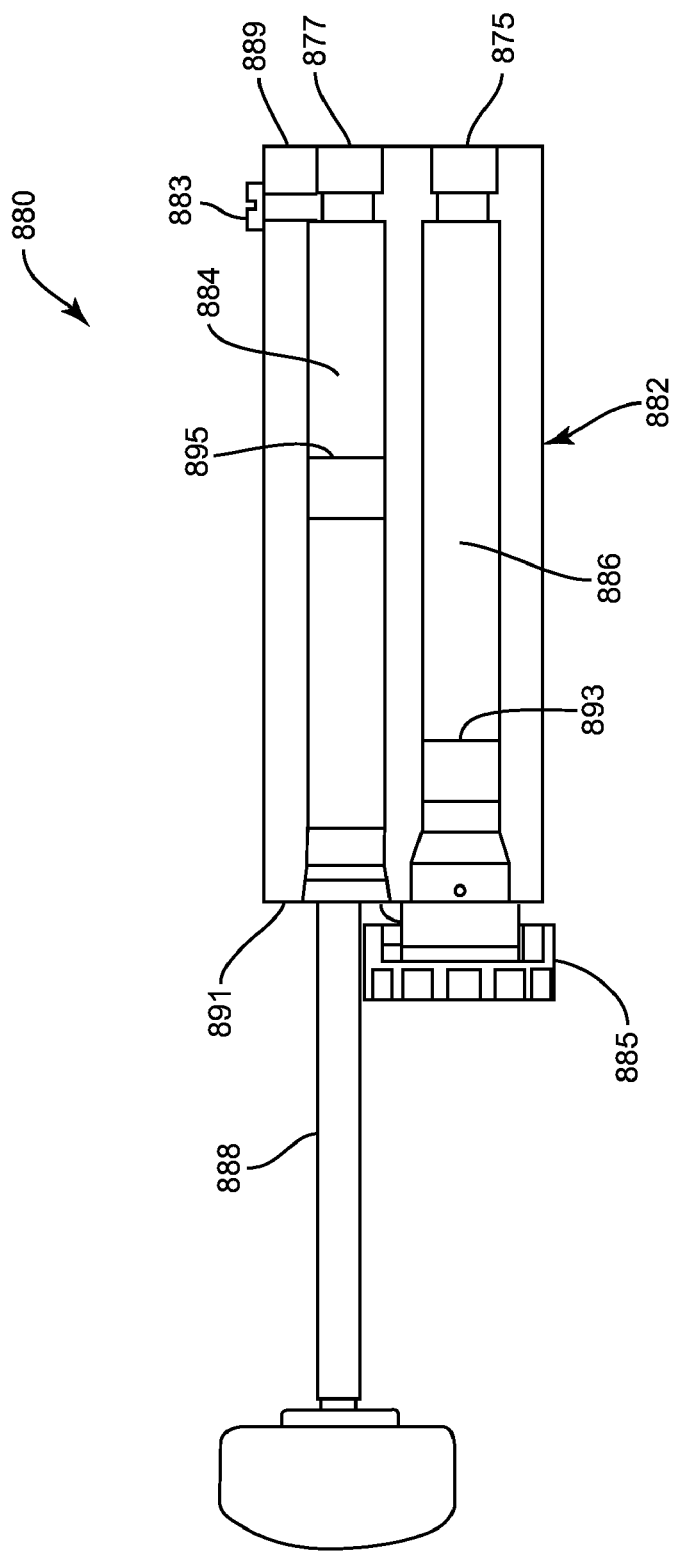
FIG. 28 is a side view of the syringe device of FIG. 25 in a fourth position.

FIGS. 25-28 illustrate an embodiment of a syringe device that can be used to control the ratio of exchange between the filler material into a cavity of a bone-related structure and the deflation of an expandable member. In this embodiment, a syringe device 880 includes a body member 882 that defines a first interior region or lumen 884 and a second interior region or lumen 886. The body member 882 also defines a first opening 877 in fluid communication with the first lumen 884 and a second opening 875 in fluid communication with the second lumen 886. An actuator 888 is coupled to a first end 891 of the body member 882. The actuator 888 can be coupled to the body member 882, for example, with a quick connect fitting, a threaded coupling or with other suitable coupling structure. The actuator 888 can be releasably coupled to the body member 882 at a first position adjacent the first lumen 884 (as shown in FIGS. 27 and 28), or a second position adjacent the second lumen 886 (as shown in FIGS. 25 and 26) and can be moved between the two positions as needed.

The syringe device 880 includes a first plunger 895 disposed within the first lumen 884 and a second plunger 893 disposed within the second lumen 886. The syringe device 880 also includes a locking mechanism 885 that can be threadably coupled to the body member 882 and/or the first plunger 895 or the second plunger 893. The locking mechanism 885 can be used to prevent movement of the plungers 895 and 893, as will be described in more detail below. The first lumen 884 can receive and contain an inflation medium, and the second lumen 886 can receive and contain a filler material. As with the previous embodiment, the first plunger 895 can be actuated to move or push the inflation medium out of the first lumen 884 and into an expandable member of a medical device. The second plunger 893 can be used to move or push the filler material out of the lumen 886 and into a cavity, for example, within a bone-related structure. A delivery port 883 is coupled to the body member 882 and in fluid communication with the first lumen 884. The delivery port 883 can be used to deliver a filler material to the first lumen 884. Although not shown, a second delivery port can be coupled to the body member 882 and in communication with the second lumen 886 to deliver an inflation medium to the second lumen 886. A cap (not shown) or other device can be used to close the port 883 when desired.

The syringe device 880 also includes a cable 887 that is coupled to the first plunger 895 and to the second plunger 893. The cable 887 provides for reciprocating movement between the first plunger 895 and the second plunger 893 so that the first plunger 895 and the second plunger 893 can be actuated in concert. For example, when one of the plungers is moved distally, the other plunger will be moved proximally a controllable or predefined extent, and vise-versa.

Figure 30:
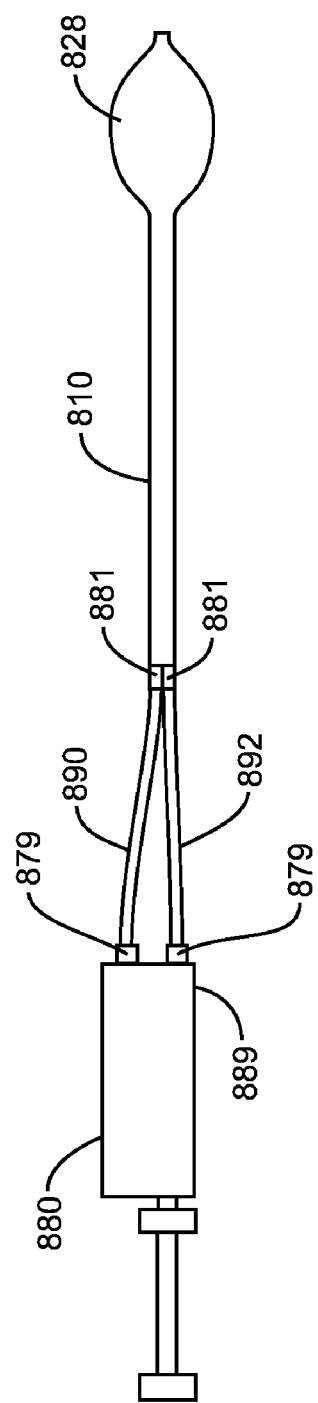
FIG. 30 is a side view of another embodiment of a syringe device.

As with the previous embodiments and as illustrated in FIG. 30, a second end 889 of the body member 882 can be coupled to a proximal end of a medical device, such as a medical device 810, via tubular members 890 and 892. The medical device 810 can include a first lumen and a second lumen (not shown) as described for previous embodiments and an expandable member or portion 828. The medical device 810 can be coupled to the tubular members 890 and 892 using fittings 881, such as, for example, luer fittings as described previously. Likewise, the syringe device 880 can be coupled to the tubular members 890 and 892 using fittings 879. Fittings 879 can also be, for example, luer fittings or another suitable coupling device. When the medical device 810 is coupled to the syringe device 880, the lumens of the syringe device are in fluid communication with the lumens of the medical device via the tubular members.

In one example procedure to fill a cavity in a bone-related structure as described herein, an inflation medium is disposed within the second lumen 886. An example of the positions of the first and second plungers, 895 and 893, respectively, with the pre-filled inflation medium within lumen 886 is illustrated in FIG. 25. The positions of the plungers within the respective lumens will vary depending on, for example, the amount of inflation medium needed for a particular medical procedure. With the syringe device 880 coupled to a proximal end of a medical device, such as medical device 810, the second plunger 893 can be moved distally within the lumen 886 using the actuator 888. This will push or move at least a portion of the inflation medium out of the second lumen 884 and into the expandable member 828 of the medical device 810. The amount of inflation medium to be delivered into the expandable member 828 can depend on the size and configuration of the cavity in which the expandable member 828 is disposed.

FIG. 26 illustrates an example where the second plunger 893 has been moved distally to a location just beyond a mid-point of the lumen 886. After delivering the inflation medium to the expandable member, the lock mechanism 885 is tightened to prevent the proximal movement of the plunger 895. This will prevent the inflation medium from moving back into the lumen 886. Next, the filler material can be delivered through the port 883 and into the first lumen 884. The actuator 888 can then be detached from the second plunger 893 and coupled to the first plunger 895 as shown in FIG. 27. The lock mechanism 885 can then be released and the actuator 888 can be moved distally to move the first plunger 895 distally and move at least a portion of the filler material from within the first lumen 884 and into a cavity of a bone-related structure. Simultaneously with the delivering of the filler material to the cavity, a corresponding amount of inflation medium will be drawn back into the second lumen 884. As with the expandable member, the amount of filler material to be delivered will depend on the size of the cavity. In this example, the first plunger 895 is moved distally, and the second plunger 893 is moved proximally as shown in FIG. 28.

This embodiment illustrates a 1:1 exchange ratio of the filler material and withdrawal of the inflation medium. As stated previously, in other embodiments the exchange ratio can vary. For example, in some embodiments, the first lumen and the second lumen can have different diameters. The first lumen can have, for example, a smaller diameter than the second lumen such that the exchange ratio between the withdrawal of the inflation medium and the filling of the filler material is 1:1.1, 1:1.2, etc. In some embodiments, the ratio of exchange of the removal of inflation medium and the delivery of filler material can be, for example, 1.1:1, 1.2:1, etc.

Figure 29:
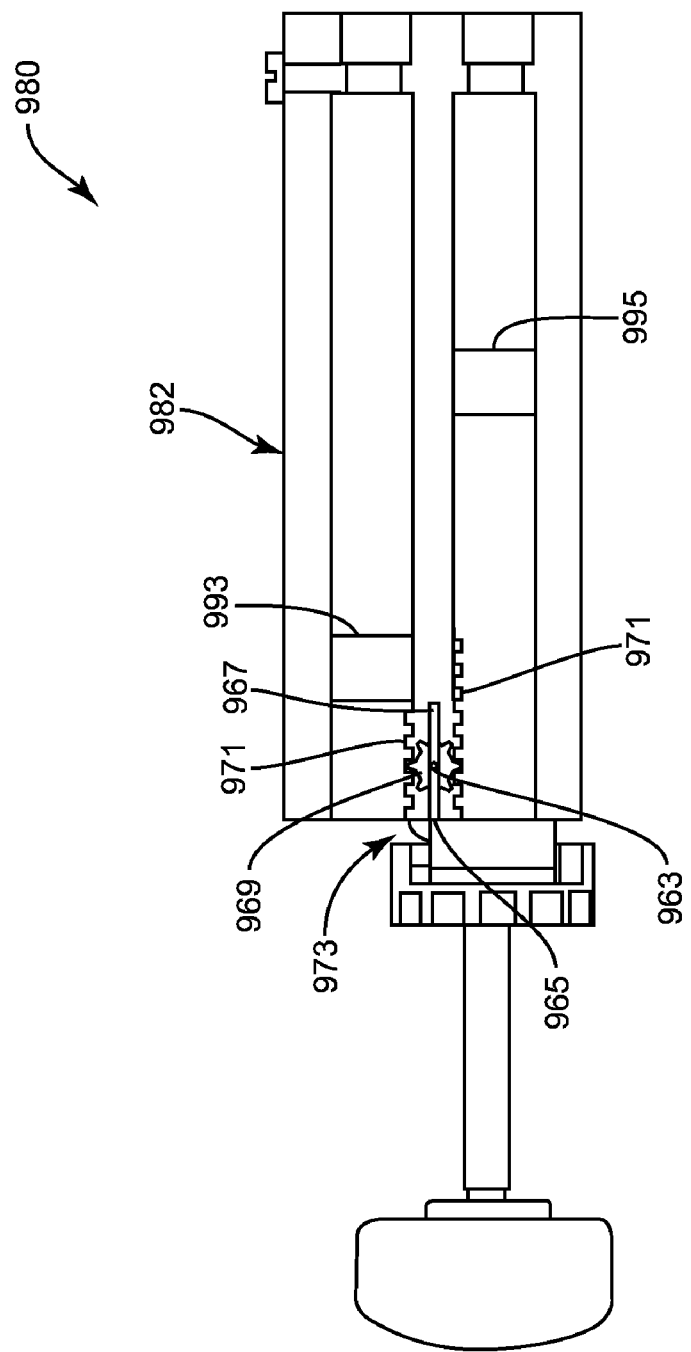
FIG. 29 is a side view of an embodiment of a medical device and the syringe device of FIGS. 25-28.

FIG. 29 illustrates another embodiment of a syringe device that includes a gear mechanism that can be used to actuate the reciprocating movement between the first and second plungers. In this embodiment, the plungers can be used in concert as described above, or can be used separately. A syringe device 980 is similarly constructed as the previous syringe device, except as stated above, the syringe device 980 includes a gear mechanism 973. The syringe device 980 includes a body member 982 that can be coupled to a medical device (e.g., 110, 210, 310, 410, etc.) as described herein, and can be used in a similar manner as previously described. The syringe device 980 also includes a first plunger 993 and a second plunger 995.

The gear mechanism 973 includes gear teeth portions 971 of the first plunger 993 and a gear teeth portion 971 of the second plunger 995. The gear teeth portions 971 can be monolithically formed with the plungers 993 and 995, or formed as separate members and coupled to the plungers 993 and 995. The gear mechanism 973 also includes a drive gear 969, such as a spur gear, that can be moved between a first position in which the gear 969 is engaged with each of the gear teeth portions 971 (as shown in FIG. 29), and a second position (not shown) in which the drive gear 969 is moved out of engagement with the gear teeth portions 971. The gear mechanism 973 includes a lever 967 coupled to the drive gear 969 and that can be used to rotate or move the drive gear 969 between the first and second positions. For example, the lever 967 can be moved or pivoted outwardly at pivot point 965 to move the drive gear 969 into the second position (i.e., disengaged position).

As stated above, in this embodiment, each of the plungers (993, 995) can be used separately, or can be used in a reciprocating manner as previously described. Thus, the gear mechanism 973 allows for the plungers (993, 995) to be disengaged to be used separately when the drive gear 969 is in the second position. When the drive gear 969 is in the first position, the plungers 993 and 995 can be used in the same manner as described above for the previous embodiment to provide a predefined ratio of exchange between the delivery of a filler material and withdrawal of an inflation medium. In use, the actuator 988 can be moved proximally or distally, which causes the drive gear 969 to turn and move the plungers 993 and 995 via the gear teeth portions 971. For example, with the actuator 988 coupled to the second plunger 995 as shown in FIG. 29, if the actuator 988 is moved proximally, the drive gear 969 will rotate in a clockwise direction, the second plunger 995 will be moved proximally and the first plunger 993 will be moved distally. If the actuator 988 is moved distally, the drive gear 969 will rotate counter-clockwise, the second plunger 995 will be moved distally and the first plunger 993 will be moved proximally.

In an alternative embodiment (not shown), the syringe device 980 can be configured without an actuator 988. In such an embodiment, a second lever (not shown) can be coupled to the drive gear 969 that extends outwardly and perpendicular from a side of the syringe device 980 when the drive gear 969 is in the first position (i.e., engaged position). The second lever can be used to manually rotate the drive gear 969 and, in turn, move the first plunger 993 and the second plunger 995 proximally and/or distally. In another alternative embodiment, the gear mechanism can include, additional gears that engage the drive gear 969 and the plungers 993 and 995. For example, a first gear (not shown) can be coupled to and engage with the gear teeth portion 971 of the plunger 993, and a second gear (not shown) can be coupled to and engage with the gear teeth portion 971 of the plunger 995 and the teeth of first gear. In such an embodiment, the first and second gears can each have a different size so as to effect a different rate of exchange between the delivery of a filler material and the withdrawal of an inflation medium.

Various other devices and components can be included in a syringe device to provide the reciprocating motion of the first and second plungers. In addition, in alternative embodiments of any of the dual lumen syringe devices described herein, the first lumen and/or the second lumen can be defined or formed by a different component of the syringe device and coupled to the body member. For example, a first and second cylindrical or tubular bodies can be coupled to the body member. In some embodiments, the syringe device does not include a body member, rather the syringe device includes two cylindrical or tubular bodies coupled together. Any of the features described above for the various embodiments of a syringe device can be included in any of the embodiments.

Figure 31:
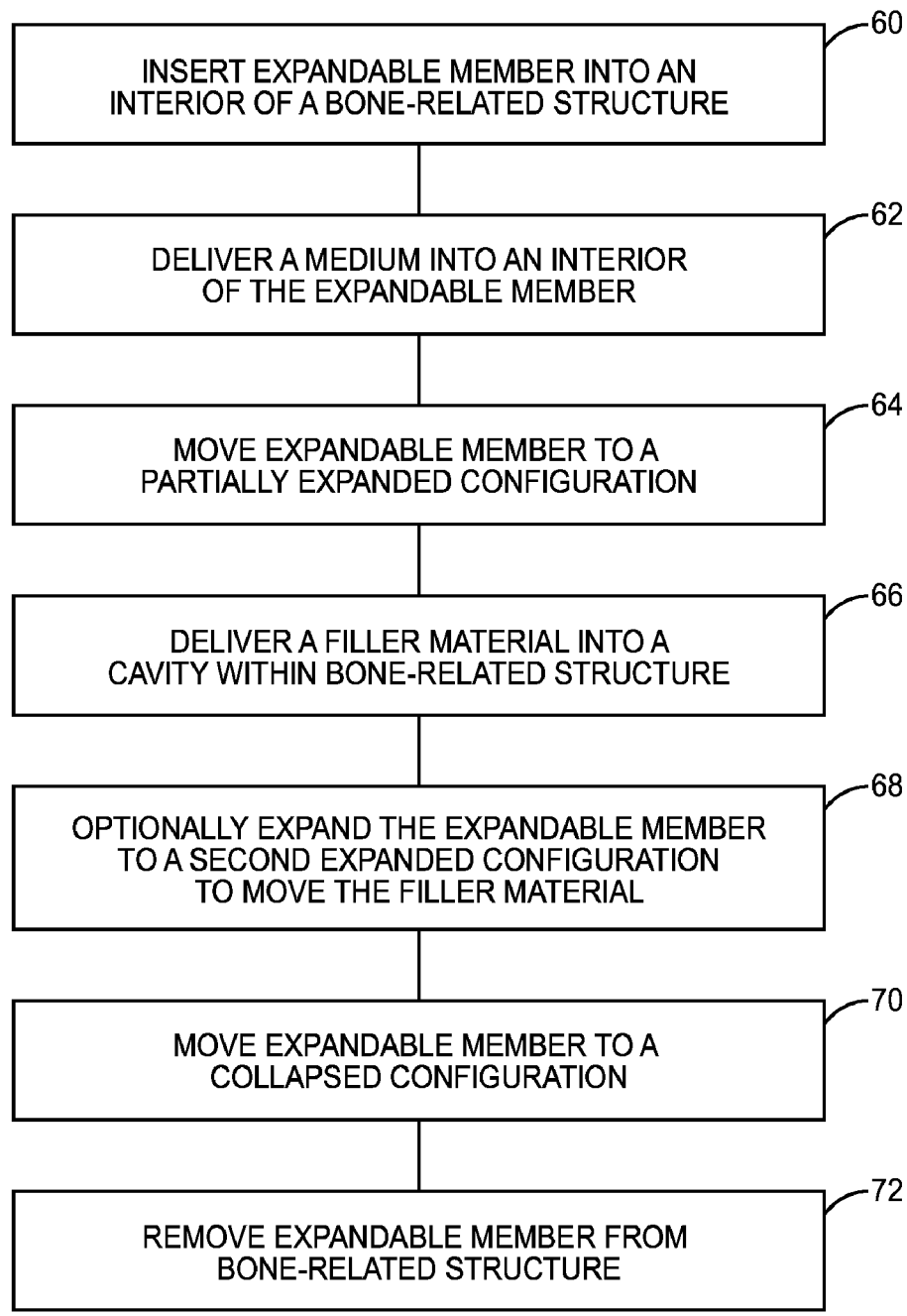
FIG. 31 is a flowchart illustrating a method according to an embodiment of the invention.

FIG. 31 is a flowchart of a method according to an embodiment of the invention. At 60, an expandable member is inserted into an interior of a bone-related structure, such as a vertebra or an intervertebral disc. The expandable member defines a first lumen and a second lumen. At 62, a medium is delivered through the first lumen and into the interior of the expandable member while the expandable member is disposed within the interior of the bone-related structure. The delivering the medium moves the expandable member from a collapsed configuration to an expanded configuration. A filler material is delivered through the second lumen and into a cavity within the interior of the bone-related structure while the expandable member is disposed therein.

In some embodiments, after the delivering the medium through the first lumen, at 64 the expandable member is moved to a partially expanded configuration in which an interior volume of the expandable member is smaller than an interior volume of the expandable member when in the expanded configuration. At 66, a filler material can be delivered through the second lumen and into a cavity within the interior of the bone-related structure while the expandable member is disposed within the interior of the bone-related structure. In some embodiments, the moving the expandable member to a partially expanded configuration as described at 64, is during at least a portion of the same time period as the delivering of the filler material. At 68, after delivering the filler material, the expandable member can optionally be expanded to a second expanded configuration to move at least a portion of the filler material. The expandable member can be moved to a collapsed configuration at 70, and removed from the bone-related structure at 72.

Figure 32:
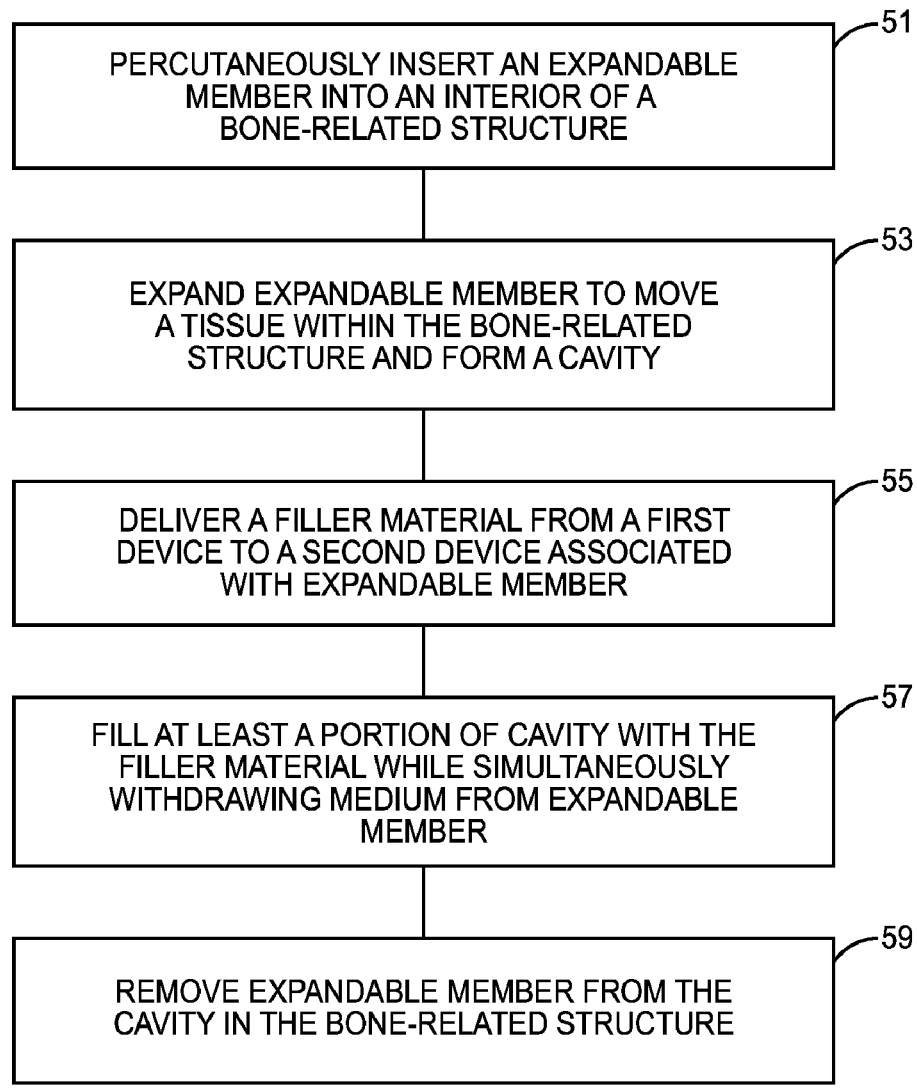
FIG. 32 is a flowchart illustrating another method according to the invention.
Figure 33:
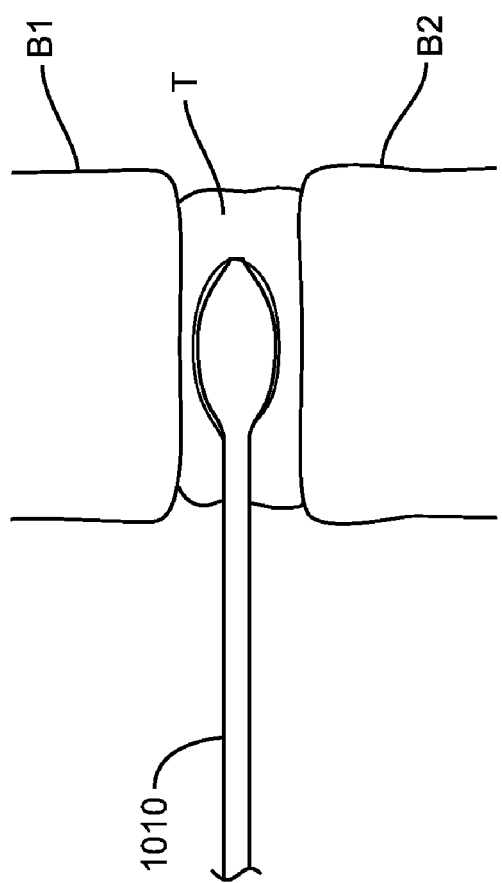
FIG. 33 is a side view of an embodiment of a medical device disposed in tissue between two bone structures.

FIG. 32 is a flowchart of another method. At 51, an expandable member in a collapsed configuration is percutaneously inserted into an interior of a bone-related structure. At 53, the expandable member is expanded with a medium to move a tissue portion and form a cavity within the interior of the bone-related structure. At 55, the filler material is delivered from a first device to a second device associated with the expandable member. At 57, at least a portion of the cavity is filled with a filler material while simultaneously withdrawing the medium from the expandable member at a predefined ratio such that the tissue portion substantially maintains its moved position. For example, in some embodiments the predefined ratio is 1:1. In some embodiments, the filling can include delivering the filler material through an opening defined in the expandable member. In other embodiments, the filling can include delivering the filler material through an opening defined in an elongate body coupled to the expandable member. At 59, the expandable member is removed from the cavity within the interior of the bone-related structure.

The devices and methods described herein may also be used in bone grafting or fusion in the spine. In such methods, the expandable member is placed within an interior of a bone-related structure to form a cavity in or near, for example, the intervertebral disc space, endplates of the vertebral body, or on and/or between the transverse processes of the spine, or any other bone-related structure where fusion or bone grafting is desired. Filler material may be delivered to the cavity or site of the desired fusion. The filler material can be, for example, bone graft materials, such as the bone graft materials described below. Delivery of bone graft materials to a particular tissue or cavity can be performed with the devices and methods described herein.

For example, in a procedure to fuse two adjacent vertebra, the surface of an endplate of an inferior vertebra and the surface of an endplate of a superior endplate can be scored (e.g., scratched, etched). A medical device as described herein can be inserted into an interior of an intervertebral disc between the two adjacent vertebra. The medical device can be actuated as described herein. For example, an expandable member can be expanded to produce an interior cavity within the intervertebral disc. A filler material, such as bone graph or bone chips can be delivered into the interior cavity in a similar manner as described above for other embodiments. For example, the filler material can be delivered at a 1:1 exchange ratio with the removal of an inflation medium from the expandable member. Bone growth can then occur between the endplates of the adjacent vertebra and the filler material disposed within the interior cavity of the intervertebral disc.

In another example, the medical devices described herein can be used between two adjacent bone structures, for example, to fuse the two bone structures. For example, as shown in FIG. 32, a medical device 1010 as described herein can be inserted between two adjacent bone structures B1 and B2, and expanded such that tissue T (e.g., soft tissue, ligaments, muscle, etc.) between the two bone structures is distracted or moved, and a cavity is formed. While maintaining the distracted position of the tissue, a filler material, such as a bone graph material, is injected into the cavity as described above for previous embodiments. The bone graph material can then fuse with the two adjacent bones. In some embodiments, a device such as a curette can be used prior to distracting the tissue, to prepare the surface of the bones for fusion.

As described above, various medical procedures can be performed using the medical devices described herein. The medical devices for any of the embodiments can be constructed with any suitable material used for such medical devices. For example, the medical devices can each be formed with biocompatible materials, such as stainless steel, or suitable plastic materials, such as various polymers, or combinations thereof. The expandable member (e.g., balloon) and the elongate body (in embodiments where the elongate body is formed with an expandable material) can be formed with various flexible or expandable materials such as plastics (e.g., various polymers) and/or rubber materials having flexible or expandable characteristics. The inflation medium can be, for example, water or a saline solution. The inflation medium can also include a contrast medium to enable viewing of the inflation medium via an X-ray or other imaging device. The filler material can be various different types of materials, such as, for example, various polymers, polyurethanes, hydrogels, or adhesives, or other nucleus replacement materials, or bone cement materials, such as PMMA, calcium phosphate, or combinations thereof. The filler material can be, for example, a material, such as those described in U.S. Pat. No. 6,692,563, or U.S. patent application Ser. No. 11/214,151 (U.S. Application Publication No. 2007/048382), the disclosures of which are hereby incorporated by reference in their entirety. The filler material can also include known bone graft materials including, for example, autograft or allograft bone materials, bone stimulating proteins (natural, synthetic or recombinant) such as the bone morphogenic proteins (e.g., BMP-2 or BMP-7), demineralized bone matrix, tissue materials, and the like.

While various embodiments of the invention have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain of the steps may be performed concurrently in a parallel process when possible, as well as performed sequentially as described above. The embodiments have been particularly shown and described, but it will be understood that various changes in form and details may be made.

For example, although the above methods have been described with reference to procedures within a vertebra or intervertebral disc, the above methods and devices can be used in other bone-related structures of a patient's body. A medical device (e.g., 10, 110, 210, 310, etc.) can include any combination or sub-combination of the various features described herein. In addition, other types of expandable devices can be used in place of, or in combination with, a balloon-type expandable member (e.g., 28, 128, 228, 328, etc.) described herein. For example, a mechanical expandable device can be used, such as a membrane-covered scissor-jack as described in U.S. patent application Ser. No. 11/095,613 (U.S. Application Publication No. 2006/0235423), or a device as described in U.S. patent application Ser. No. 11/042,546 (U.S. Application Publication No. 2005/0143827), or a device as described in U.S. patent application Ser. No. 11/454,153 (U.S. Application Publication No. 2007/0043361), the disclosures of which are hereby incorporated by reference in their entirety. An expandable member as described herein can be used in conjunction with a mechanical device that is disposed within an interior of the expandable member and used to expand the expandable member.

The expandable members can also be a variety of different shapes and sizes, such as, for example, expandable devices described in U.S. Pat. No. 5,972,015, and U.S. Pat. No. 6,981,981, the disclosures of which are hereby incorporated by reference in their entirety. The medical devices described herein can define lumens having various shapes, sizes and configurations, such as those described in U.S. patent application Ser. No. 11/124,387 (U.S. Application Publication No 2006/0264896), the disclosure of which is hereby incorporated by reference in its entirety. For example, a cross-section of a lumen can be circular, square, oval, elliptical, triangular, oblong, curved, angled, etc. Moreover, the position of the first lumen relative to the second lumen can vary from the example embodiments described herein. Although not specifically illustrated, any of the embodiments of a medical device can optionally include a seal member (e.g., 146, 246).

What is claimed is:

1. A method, comprising:
    expanding an expandable member with a medium to move a tissue portion and form a cavity within an interior of a bone-related structure;
    filling at least a portion of the cavity with a filler material while simultaneously withdrawing the medium from the expandable member at a predefined ratio such that the tissue portion substantially maintains its moved position, and
    expanding the expandable member to a second configuration to move at least a portion of the filler material while the expandable member is disposed within the interior of the bone-related structure,
    wherein the expandable member is sufficiently flexible such that as the filler material is being delivered into the cavity the expandable member is compressed by the filler material thereby disposing the filler material around an exterior of the expandable member.

2. The method of claim 1, wherein the predefined ratio is 1:1.

3. The method of claim 1, wherein the expandable member is coupled to a syringe device configured to deliver the filler material to the cavity of the bone-related structure while simultaneously withdrawing the medium from the expandable member.

4. The method of claim 1, wherein the filling includes delivering the filler material through an opening defined in the expandable member.

5. The method of claim 1, wherein the filling includes delivering the filler material through an opening defined in an elongate body coupled to the expandable member.

6. The method of claim 1, further comprising: delivering the filler material from a first device to a second device associated with the expandable member.

7. The method of claim 1, wherein the filler material is a bone cement.

8. The method of claim 1, wherein the filler material is a nucleus replacement material.

9. The method of claim 1, wherein the filler material is a bone graft material.

10. A method, comprising:
    expanding an expandable member to move a tissue portion and form a cavity within an interior of an intervertebral disc;
    filling at least a portion of the cavity with a filler material while substantially maintaining the moved position of the tissue portion, and expanding the expandable member to a second configuration to move at least a portion of the filler material while the expandable member is disposed within the interior of the bone-related structure,
wherein the expandable member is sufficiently flexible such that as the filler material is being delivered into the cavity the expandable member is compressed by the filler material thereby disposing the filler material around an exterior of the expandable member.

11. The method of claim 10, wherein the expanding is performed via a first lumen associated with the expandable member, the filling is performed via a second lumen associated with the expandable member.

12. The method of claim 10, further comprising: after the filling, moving at least a portion of the filler material within the cavity.

13. The method of claim 10, wherein during the filling, the expandable member is in an expanded configuration and disposed within the interior of the intervertebral disc.

14. The method of claim 10, wherein the filling is during a time period, the method further comprising: at least partially deflating the expandable member during at least a portion of the time period.

15. The method of claim 10, wherein the filling is during a time period, the method further comprising: moving the expandable member proximally during at least a portion of the time period such that at least a portion of the expandable member is removed from the cavity.

16. The method of claim 10, wherein the expandable member is a balloon.

17. The method of claim 10, wherein the filler material is a nucleus replacement material.

18. The method of claim 10, wherein the filler material is a bone graft material. at a predefined ratio such that the tissue portion substantially maintains its moved position.

19. The method of claim 10, further comprising: withdrawing a medium from the expandable member substantially simultaneously with the filling the cavity with a filler material such that the withdrawing and the filling is performed at a predefined exchange ratio.

* * * * *